(12) United States Patent
Pevzner et al.

(10) Patent No.: US 8,457,900 B2
(45) Date of Patent: Jun. 4, 2013

(54) METHOD FOR IDENTIFICATION AND SEQUENCING OF PROTEINS

(75) Inventors: Pavel A. Pevzner, La Jolla, CA (US); Nuno F. C. Bandeira, La Jolla, CA (US); Dekel Tsur, Be'er Sheva (IL)

(73) Assignee: The Regents of the University of California, Oakland, CA (US)

( * ) Notice: Subject to any disclaimer, the term of this patent is extended or adjusted under 35 U.S.C. 154(b) by 1007 days.

(21) Appl. No.: 12/279,836

(22) PCT Filed: Mar. 22, 2007

(86) PCT No.: PCT/US2007/064722
§ 371 (c)(1),
(2), (4) Date: Aug. 18, 2008

(87) PCT Pub. No.: WO2007/112289
PCT Pub. Date: Oct. 4, 2007

(65) Prior Publication Data
US 2011/0015863 A1    Jan. 20, 2011

Related U.S. Application Data

(60) Provisional application No. 60/785,960, filed on Mar. 23, 2006.

(51) Int. Cl.
G01N 33/48    (2006.01)
G01N 31/00    (2006.01)
G01B 3/00     (2006.01)
G06F 7/60     (2006.01)
G06F 19/00    (2006.01)

(52) U.S. Cl.
CPC .................................. G06F 19/00 (2013.01)
USPC ...................... 702/19; 702/22; 702/27; 703/2

(58) Field of Classification Search
None
See application file for complete search history.

(56) References Cited

U.S. PATENT DOCUMENTS

| | | | |
|---|---|---|---|
| 5,547,835 A | 8/1996 | Koster | |
| 5,605,798 A | 2/1997 | Koster | |
| 5,849,492 A | 12/1998 | Rogan | |
| 5,965,363 A | 10/1999 | Monforte et al. | |

(Continued)

FOREIGN PATENT DOCUMENTS

| WO | WO9812355 | 3/1998 |
|---|---|---|
| WO | WO9914375 | 3/1999 |

OTHER PUBLICATIONS

Taylor et al. Sequence database searches via de novo peptide sequencing by tandem mass spectrometry. Rapid Communications is Mass Spectrometry, vol. 11, 1997, pp. 1067-1075.*

(Continued)

*Primary Examiner* — Russell S Negin
(74) *Attorney, Agent, or Firm* — Eleanor M. Musick; Procopio, Cory, Hargreaves & Savitch LLP

(57) ABSTRACT

Protein samples are processed to create a mixture of modified and unmodified or overlapping peptides which are analyzed using mass spectrometry. Correlations between the MS/MS spectra of peptide pairs allow the noise in individual MS/MS spectra to be greatly reduced. A small number of peptide reconstructions can be generated that are likely to contain the correct one. This allows for the de novo reconstruction of protein sequences and peptide and modification identification through a database search using extremely fast pattern matching, rather than time-consuming matching of spectra against databases.

22 Claims, 10 Drawing Sheets

U.S. PATENT DOCUMENTS

| | | | |
|---|---|---|---|
| 6,043,031 | A | 3/2000 | Koster et al. |
| 6,197,498 | B1 | 3/2001 | Koster |
| 6,221,601 | B1 | 4/2001 | Koster et al. |
| 6,221,605 | B1 | 4/2001 | Koster |
| 6,235,478 | B1 | 5/2001 | Koster |
| 6,258,538 | B1 | 7/2001 | Koster et al. |
| 6,277,573 | B1 | 8/2001 | Koster |
| 6,300,076 | B1 | 10/2001 | Koster |
| 6,428,955 | B1 | 8/2002 | Koster et al. |
| 6,500,621 | B2 | 12/2002 | Koster |
| 2004/0175838 | A1* | 9/2004 | Jarman et al. ............ 436/173 |
| 2004/0219601 | A1* | 11/2004 | Xu et al. ............ 435/7.1 |
| 2004/0253636 | A1* | 12/2004 | Soloviev et al. ............ 435/7.1 |
| 2006/0022129 | A1 | 2/2006 | Shchepinov et al. |

OTHER PUBLICATIONS

Bafna et al. SCOPE: a probabilistic model for scoring tandem mass spectra against a peptide database. Bioinformatics, vol. 17, 2001, pp. S13-S21.*

Janssens et al. Evaluation of three zero-area digital filters for peak recognition and interference detection in automated spectral data analysis. Analytical Chemistry, vol. 63, 1991, pp. 320-331.*

Wilkins et al. Detailed peptide characterization using PEPTIDEMASS—a World-Wide-Web-accessible tool. Electrophoresis, vol. 18, 1997, pp. 403-408.*

Ouyang et al. Tyrsosylprotein sulfotransferase: Purification and molecular cloning of an enzyme that catalyzes tyrosine O-sulfation, a common posttranslational modification of eukaryotic proteins. PNAS, vol. 95, 1998, pp. 2896-2901.*

Senko et al. Determination of monoisotopic masses and ion populations for large biomolecules from resolved isotopic distributions. Journal of the American Society for Mass Spectrometry, 1995, vol. 6, pp. 229-233.*

Chen et al. A dynamic programming approach to de novo peptide sequencing via tandem mass spectrometry. Journal of Computational Biology, vol. 8, 2001, pp. 325-337.*

International Search Report and Written Opinion for PCT/US07/64722 dated Feb. 14, 2008.

Bandeira et al., Shotgun Protein Sequencing by Tandem Mass Spectra Assembly, Analytical Chemistry, Dec. 15, 2004, vol. 76, No. 24, pp. 7221-7233.

Pevzner et al., Mutation-Tolerant Protein Identification by Mass Spectrometry, Journal of Computational Biology, Dec. 2000, vol. 7, No. 6, pp. 777-787.

Bern et al, Automatic Quality Assessment of Peptide Tandem Mass Spectra, Bioinformatics vol. 20 (Suppl.1) 2004, pp. i49-i54, Oxford University Press 2004, Jan. 15, 2004, Palo Alto Research Center, CA and The Scripps Research Institute, CA.

Bandeira et al., Shotgun Protein Sequencing, Molecular & Cellular Proteomics 6:1123-1134, downloaded from www.mcponline.org at UCSD, Oct. 24, 2007, La Jolla, CA 92093.

Bandeira et al., Protein Identification by Spectral Networks Analysis, PNAS, Apr. 10, 2007, 6140-6415, vol. 104, No. 15, Dept. fo Computer Science and Engineering, UCSD, La Jolla, CA 92093.

de Souza, Natalie, et al., Mining for Natural Products, Nature Methods/Research Highlights, Jun. 2007, p. 470-471, vol. 4 No. 6.

Dancik, Vlado, et al., De Novo Peptide Sequencing via Tandem Mass Spectrometry, Journal of Computational Biology, 1999, pp. 327-342, vol. 6, Nos. 3/4, Mary Ann Liebert, Inc.

Frank, Ari, et al., Peptide Sequence Tags for Fast Database Search in Mass-Spectrometry, Journal of Proteome Research 2005, pp. 1287-1295, vol. 4, No. 4, Dept. f Computer Science & Engineering, UCSD, La Jolla, CA 92093-0419, Jun. 15, 2005.

Frank, Ari, et al., PepNovo: De Novo Peptide Sequencing via Probabilistic Network Modeling, Analytical Chemistry, vol. 77, No. 4, Feb. 15, 2005, pp. 964-973, Dept. of Computer Science & Engineering, UCSD, La Jolla, CA 92093.

Pevzner, Paul A. et al., De Novo Repeat Classification and Fragment Assembly, Genome Research, 2004 14: 1786-1796, Dept. of Computer Science and Engineering and Dept. of Mathematics, UCSD, La Jolla, CA, 92093, USA, Cold Spring Harbor Laboratory Press.

Tsur, D. et al., Identification of Post-Translational Modification by Blind Search of mass Spectra, Nature Biotechnology, Dec. 2005; 23(12): 1562-7, Dept. of Computer Science & Engineering, UCSD, La Jolla, CA 92093.

Smith, T.F et al., Identification of Common Molecular Subsequences, Reprinted from J. Mol. Biol. (1981), 147, 195-197, 1980 Academic Press, Inc. (London) Ltd.

Tanner, Stephen, et al., InsPecT: Identification of Posttranslationally Modified Peptides from Tandem Mass Spectra, Analytical Chemistry, vol. 77, No. 14, Jul. 15, 2005, Dept. of Bioengineering and Computer Science Department, APM 3832, et al.,UCSD, La Jolla, CA 92093-0114.

Tanner, Stephen, et al., Unrestrictive identification of post-translational modifications through peptide mass spectrometry, Nature Protocols, vol. 1 No. 1, pp. 67-72, 2006, Nature Publishing Group.

Ben-Dor, Amir, et al., Clustering Gene Expression Patterns, Hewlett-Packard Laboratories Israel, Technion City, HPL-98-190, Nov. 4, 1998, pp. 1-12, Copyright Hewlett-Packard Company 1998, Haifa 32000 Israel.

Chen, Ting, et al., A Dynamic Programming Approach to De Novo Peptide Sequencing via Tandem Mass Spectrometry, J. Comput. Biol. 2001; 8(3): 325-37.

* cited by examiner

Figure 1a  Figure 1b

1 KQGGTLDD   LEE   QAREL
2 KQGGTLDD   LEE   QARE
3 KQGGTLDD   LEE   QAR
4 KQGGTLDD   LEE   QA
5 KQGGTLDD   LEE$^{-18}$ QAR
6 KQGGTLDD   LEE$^{-18}$ Q
7  QGGTLDD   LEE   QAR
8  QGGTLDD$^{+53}$ LEE   QAR

| Type # | Type of jump | Usage | Sequence Alignment Analogy |
|---|---|---|---|
| 1 | Horizonal/Vertical jumps at top-left and bottom-right corners | Modeling different prefixes/suffixes | Terminal gaps |
| 2 | Diagonal jumps | Modeling the same mass difference between matched peaks | Matching characters |
| 3 | Oblique jumps | Modeling modifications of mass $\delta$ | Internal gap of width $\delta$ |

US 8,457,900 B2

METHOD FOR IDENTIFICATION AND SEQUENCING OF PROTEINS

RELATED APPLICATIONS

This application claims the benefit of the priority of U.S. provisional application No. 60/785,960, filed Mar. 23, 2006, which is incorporated herein by reference in its entirety.

GOVERNMENT RIGHTS

This invention was made with government support under RR16522 awarded by the National Institutes of Health. The government has certain rights in the invention.

FIELD OF THE INVENTION

The present invention is generally directed to protein identification methods and is particularly concerned with a system and method for identification of peptides and post-translational modifications.

BACKGROUND OF THE INVENTION

Most protein identifications today are performed by matching spectra against databases using programs like SEQUEST or MASCOT. While these tools are invaluable, they are already too slow for matching large MS/MS datasets against large protein databases. Recent progress in mass spectrometry instrumentation (a single LTQ-FT mass-spectrometer can generate 100,000 spectra per day) may soon make them obsolete. Since SEQUEST compares every spectrum against every database peptide, it will take a cluster of about 60 processors to analyze the spectra produced by a single such instrument in real time (if searching through the Swiss-Prot database). If one attempts to perform a time-consuming search for post-translational modifications, the running time may further increase by orders of magnitude. New solutions are needed to deal with the stream of data produced by shotgun proteomics projects. Algorithms have recently been developed that prune (X!Tandem) and filter (InsPecT) (see Tanner et al., *Anal Chem.*, 77(14):4626-39, Jul. 15, 2005, (incorporated herein by reference)) databases to speed-up the search. However, these tools still require comparison of every spectrum against the smaller database.

Moreover, the common assumption that all proteins of interest are present in the database is often refuted by the limited availability of sequenced genomes and multiple mechanisms of protein variation. Well known mechanisms of protein diversity include variable recombination and somatic hypermutation of immunoglobulin genes. The vital importance of some of these novel proteins is directly reflected by the success of monoclonal antibody drugs such as Rituxan™, Herceptin™ and Avastin™, all derived from proteins that are not directly inscribed in any genome. Similarly, multiple commercial drugs have been developed from proteins obtained from species whose genomes are not known. In particular, peptides and proteins isolated from venom have provided essential clues for drug design—examples include drugs for controlling blood coagulation and drugs for breast and ovarian cancer treatment. Even so, the genomes of the venomous snakes, scorpions, and snails are unlikely to become available anytime soon. Despite this vital importance of novel proteins, the mainstream method for protein sequencing is still the restrictive and low-throughput Edman degradation—a task made difficult by protein purification procedures, post-translational modifications and blocked protein N-termini. These problems gain additional relevance when one considers the unusually high level of variability and post-translational modifications in venom proteins. The primary function of venom is to immobilize prey and prey animals vary in their susceptibility to venom. As a result, venom composition within snake species shows considerable geographical variation, an important consideration because snake bites (even by snakes of the same species) may require different treatments. Moreover, the amount and number of different proteins and isoforms varies with gender, diet, etc.

Mass spectrometry provides detailed information about the molecules being analyzed, including high mass accuracy. It is also a process that can be easily automated. However, high-resolution MS alone fails to perform against unknown or bioengineered agents, or in environments where there is a high background level of bioagents ("cluttered" background). Low-resolution MS can fail to detect some known agents, if their spectral lines are sufficiently weak or sufficiently close to those from other peptides in the sample. DNA chips with specific probes can only determine the presence or absence of specifically anticipated peptides. Because there are hundreds of thousands of species of benign bacteria, some very similar in sequence to threat organisms, even arrays with 10,000 probes lack the breadth needed to detect a particular organism.

Antibodies face more severe diversity limitations than arrays. If antibodies are designed against highly conserved targets to increase diversity, the false alarm problem will dominate, again because threat organisms are very similar to benign ones. Antibodies are only capable of detecting known agents in relatively uncluttered environments.

Reports have described detection of PCR products using high resolution electrospray ionization—Fourier transform—ion cyclotron resonance mass spectrometry (ESI-FT-ICR MS). Accurate measurement of exact mass combined with knowledge of the number of at least one nucleotide allowed calculation of the total base composition for PCR duplex products of approximately 100 base pairs. (Aaserud et al., *J. Am. Soc. Mass Spec.* 7:1266-1269, 1996; Muddiman et al., *Anal. Chem.* 69:1543-1549, 1997; Wunschel et al., *Anal. Chem.* 70:1203-1207, 1998; Muddiman et al., *Rev. Anal. Chem.* 17:1-68, 1998). Electrospray ionization-Fourier transform-ion cyclotron resistance (ESI-FT-ICR) MS has been used to determine the mass of double-stranded, 500 base-pair PCR products via the average molecular mass (Hurst et al., *Rapid Commun. Mass Spec.* 10:377-382, 1996). The use of matrix-assisted laser desorption ionization-time of flight (MALDI-TOF) mass spectrometry for characterization of PCR products has been described. (Muddiman et al., *Rapid Commun. Mass Spec.* 13:1201-1204, 1999). However, the degradation of DNAs over about 75 nucleotides observed with MALDI limited the utility of this method.

U.S. Pat. No. 5,849,492 describes a method for retrieval of phylogenetically informative DNA sequences which comprise searching for a highly divergent segment of genomic DNA surrounded by two highly conserved segments, designing the universal primers for PCR amplification of the highly divergent region, amplifying the genomic DNA by PCR technique using universal primers, and then sequencing the gene to determine the identity of the organism.

U.S. Pat. No. 5,965,363 discloses methods for screening nucleic acids for polymorphisms by analyzing amplified target nucleic acids using mass spectrometric techniques and to procedures for improving mass resolution and mass accuracy of these methods.

WO 99/14375 describes methods, PCR primers and kits for use in analyzing preselected DNA tandem nucleotide repeat alleles by mass spectrometry.

WO 98/12355 discloses methods of determining the mass of a target nucleic acid by mass spectrometric analysis, by cleaving the target nucleic acid to reduce its length, making the target single-stranded and using MS to determine the mass of the single-stranded shortened target. Also disclosed are methods of preparing a double-stranded target nucleic acid for MS analysis comprising amplification of the target nucleic acid, binding one of the strands to a solid support, releasing the second strand and then releasing the first strand which is then analyzed by MS. Kits for target nucleic acid preparation are also provided.

PCT WO97/33000 discloses methods for detecting mutations in a target nucleic acid by non-randomly fragmenting the target into a set of single-stranded nonrandom length fragments and determining their masses by MS.

U.S. Pat. Nos. 5,547,835, 5,605,798, 6,043,031, 6,197,498, 6,221,601, 6,221,605, 6,277,573, 6,235,478, 6,258,538, 6,300,076, 6,428,955 and 6,500,621, describe fast and highly accurate mass spectrometer-based processes for detecting the presence of a particular nucleic acid in a biological sample for diagnostic purposes.

WO 98/20166 describes processes for determining the sequence of a particular target nucleic acid by mass spectrometry. Processes for detecting a target nucleic acid present in a biological sample by PCR amplification and mass spectrometry detection are disclosed, as are methods for detecting a target nucleic acid in a sample by amplifying the target with primers that contain restriction sites and tags, extending and cleaving the amplified nucleic acid, and detecting the presence of extended product, wherein the presence of a DNA fragment of a mass different from wild-type is indicative of a mutation. Each of the publications and patent documents cited herein is incorporated herein by reference.

One algorithmic approach recognized the conserved regions of genomic space. Regions of variability flanked these conserved regions. Although the nucleotide sequence of the variable region was unknown, the understanding of the conserved regions, together with the absolute limitation on nucleotide options (A,C,T,G,U) simplified the list of potential sequences, based on molecular weight.

Each of the foregoing require substantial understanding of the peptide of concern. In many cases specific PCR primers and/or molecular tags are required. It is clear there is a need for an algorithmic method for identifying a peptide without the foregoing limitations.

SUMMARY OF THE INVENTION

It is an object of the present invention to provide a new and improved method of interpreting peptides, proteins and post-translational modifications on tandem mass spectrometry data from biological samples.

According to one aspect of the invention, a method of peptide identification is provided in which an experimental protocol is changed in order to generate many modified peptides, creating a large number of "spectral pairs" that open up computational approaches for analysis. A "spectral pair" is the spectrum of a modified peptide paired with the spectrum of an unmodified peptide or two spectra from overlapping peptides. The use of spectral pairs allows separation of the suffix and prefix mass ladders to greatly reduce the number of noise peaks, and to generate a small number of peptide reconstructions that are likely to contain the correct one. A computational analysis is carried out to detect and combine MS/MS spectra from related peptides and to construct longer amino acid sequence tags, which are then matched to a database of sequences using text matching techniques to identify the peptides and amino acid modifications in the analyzed sample.

This technique allows an MS/MS database search to be performed without comparing a spectrum against a database. The method includes two components: experimental and computational. The experimental component, while contrary to normal practice, is trivial to implement. The experimental protocol is modified by intentionally introducing chemical damage to the sample and generating many modified peptides. Current protocols attempt to achieve the opposite goal of minimizing the chemical damage since (i) modified peptides are difficult to interpret and (ii) chemical adducts do not provide any useful information.

From the experimental perspective, subjecting a sample to chemical damage does not make any sense. However, from the computational perspective, it creates a large number of "spectral pairs" that open up computational avenues not previously explored. One technique which may be used to chemically damage the sample is to warm it up in urea solution or to simply bring it into mildly acidic pH and add a hefty concentration of hydrogen peroxide. One exemplary method for creating a mixture of modified and unmodified peptides is to split a sample into two parts, chemically damage one part, and combine both parts together again. This produces spectral pairs, each pair comprising a modified peptide and an unmodified peptide. In contrast to previous approaches creating sets of short 3-4 amino acid tags, the present invention generates a small covering set of peptides 7-9 amino acids long. This set typically has a single perfect hit in the database that can be instantly found by hashing and thus eliminates the need to compare the spectrum against the database.

In one aspect of the invention, a protein sequence interpretation is performed using a combination of spectra from different (and possibly modified and mutated) peptides using the following steps: providing a sample comprising a plurality of proteins; if necessary, processing the sample to obtain peptide pairs; obtaining a spectrum for each peptide of the peptide pair to produce a spectral pair; comparing the spectra for the spectral pair to separate signal/noise peaks within the spectra; removing the noise peaks; generating a de novo sequence reconstruction. If a database is available, conducting a database search using the peptide reconstruction.

In another aspect of the invention, protein modifications are discovered without a sequence database using the steps of: providing a sample comprising a plurality of proteins; if necessary, processing the sample to obtain peptide pairs; obtaining a spectrum for each peptide of the spectral pair; comparing the spectra for the spectral pair to separate signal/noise peaks within the spectra; removing the noise peaks; generating a consensus peptide reconstruction; finding the protein modifications by listing all the differences between the consensus peptide reconstruction and the sequence variants detected by spectral pairs.

Possible processing strategies for generating the peptide pairs include, but are not limited to digesting the proteins with one or more enzymes or reagents; and introducing artifactual modifications—these are an almost unavoidable outcome of common sample handling procedures. Further, most protein samples already include multiple modified and overlapping variants of the same peptides.

The present invention provides an improved method for protein identification over known tools by eliminating the need to compare a spectrum against a database. Instead, the method of this invention allows for the determination of amino acid sequence tags from tandem mass spectrometry spectral pairs and subsequent peptide and modification identification through a database search using extremely fast pattern matching. The method is useful for anyone interested in identifying peptides, proteins, and post-translational modifications from biological samples.

BRIEF DESCRIPTION OF THE DRAWINGS

FIG. 1 illustrates the spectral product of the peptides of TEVMA and TEVMAFR where FIG. 1a shows the spectral product for the theoretical spectra of these peptides; FIG. 1b shows the spectral product for uninterpreted spectra of the peptides.

DETAILED DESCRIPTION OF THE INVENTION

Figure 1C:
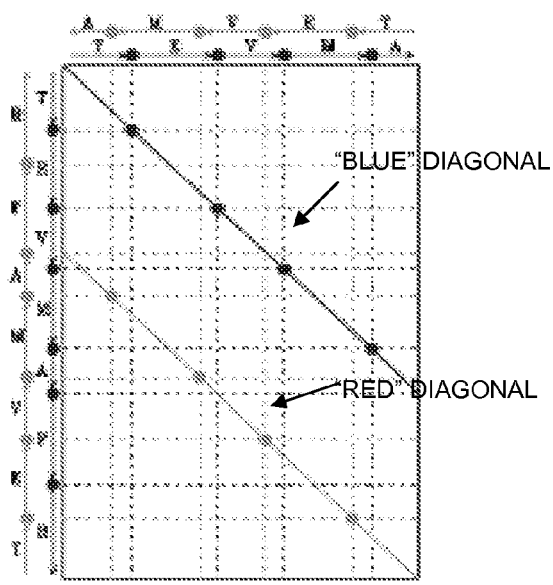
FIG. 1c illustrate how the two diagonals define the spectra.
Figure 1C:
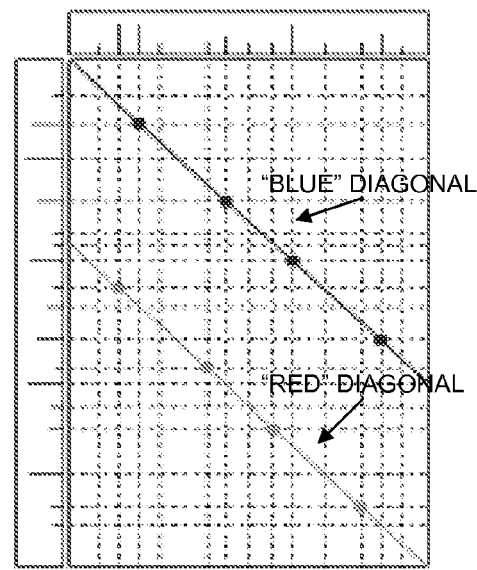
Figure 1C:
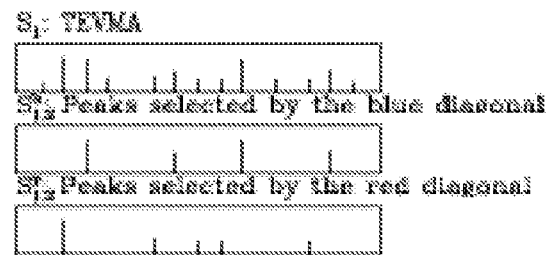
Figure 1C:
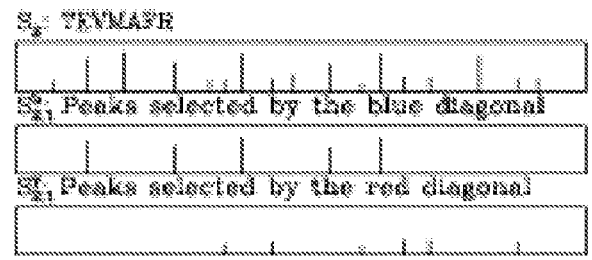

This invention is directed to a method of performing a MS/MS database search without requiring comparison of a spectrum against a database of spectra. The inventive method incorporates a computational component and an experimental component. In the experimental set-up, a desktop machine running the Linux operating system on an Intel® Pentium® 4 CPU at a clock speed of 2.8 GHz with 1 Gb of RAM was used for the computational component. It will be readily apparent to those in the art that other processors (e.g., Apple® Macintosh®) and operating systems (e.g., Microsoft Windows®) may be adapted to execute the algorithms and generate outputs (displayed or printed) of the analysis results. Accordingly, the invention is not intended to be limited to execution by any specific processor or operating system.

Definitions: As used herein, "spectrum" is a list of numbers (e.g., amino acid masses) with associated intensities.

"Peptide" is any polymer where the sequence of monomers can be expressed as a spectrum (e.g. peptide/protein sequences).

"Sequence" is a string of symbols describing the polymer (e.g. a [possibly modified] protein sequence).

"Modification" is any observable change in the measurable property of a monomer as compared to some reference polymer. Specific examples include post-translational modifications or mutations of amino acid residues. The reference polymer can be any [possibly unknown] reference.

"Contig" is a set of overlapping spectra assembled according to the inventive method.

"Contig sequences" are de novo sequences obtained from contigs.

According to the present invention, damage is intentionally introduced to the peptides of a sample to produce many modified peptides. While this may be counterintuitive, it provides useful information regarding the identity of the peptides of the sample. The same sample is also subjected to MS/MS analysis, thereby providing a set of spectral pairs corresponding to both the modified and the unmodified peptide. Comparison of the paired spectra provides for substantial elimination of background noise. The resulting spectra allow generation of a small list of potential peptide sequences that correlate to both the modified and un-modified spectra, one of which is very likely the correct one.

Seemingly regardless of modification technique, peptides of a sample that are modified through one or more identical techniques will undergo correspondingly similar modifications. The modified peptides will have a modified prefix, suffix, in-between and/or a combination thereof. The selected modification technique is surprisingly consistent relative to the modification caused to each individual peptide. A chemical modifier that incorporates a specific amino acid to the 3' end of a peptide, will consistently perform a similar modification to all peptides of the sample. In a similar fashion, an enzyme that cleaves a peptide at a specific nucleotide junction will likely perform a corresponding cleavage in all peptides of the sample at the same corresponding junction. Algorithmically, this facilitates the designation of "spectral pairs." Having a pair of spectra (one of a modified and another of an unmodified peptides) allows one to separate the prefix and suffix mass spectra and thereby to greatly reduce the number of the noise peaks, and to generate small number of peptide reconstructions that are likely to contain the correct reconstruction(s).

The consensus spectrum of a cluster from multiple spectra of the same peptide contains fewer noise peaks than each individual spectra of the cluster group. Clustering, described by Pevzner et al. in *Genome Res.* 14:1786-1796, 2004, which is incorporated herein by reference, facilitates the determination of spectral pairs. Clustering leverages the fact that true peaks (as differentiated from spectral noise) occur in multiple spectra from the same peptide, while noise peaks do not. Clustering is performed by first transforming every spectrum into its scored version wherein peak intensities are substituted with log-likelihood scores, using a heuristic approach. Each cluster of spectra is then collapsed into a single consensus spectrum that contains peaks present in at least K spectra in the cluster. The parameter K is chosen in such a way that the probability of incorporating a random or false peak in the consensus spectrum by chance is below 0.01. The resulting consensus spectra have unexpectedly high signal to noise ratios.

Clustering multiple spectra of the same peptide achieves a twofold goal: (i) the consensus spectrum of a cluster contains much fewer noise peaks than the individual spectra, and (ii) clustering speeds up and simplifies the search for spectral pairs. The clustering step capitalizes on the fact that true peaks consistently occur in multiple spectra from the same peptide, while noise peaks do not. The clustering approach used for the inventive method follows the shotgun protein sequencing method described by Bandeira et al. (*Analytical Chem.* 76:7221-7233, 2004, incorporated herein by reference), with some improvements described below.

Traditional analysis of tandem mass spectra focuses on the analysis of individual MS/MS spectra instead of capitalizing on the common event of repeated MS/MS spectra for the same peptide or combining spectra from partially overlapping peptides. Shotgun Protein Sequencing is an approach to the analysis of tandem mass spectra that combines uninterpreted MS/MS spectra into ladders of overlapping spectra (multiple alignments of MS/MS spectra) before constructing a common amino acid interpretation for the whole multiple alignment.

First, every spectrum is transformed into a scored version that substitutes peak intensities with log-likelihood scores. Any scoring used in de novo peptide sequencing algorithms can be used for such transformation, however, in the preferred embodiment the method described by Frank et al. (*Analytical Chem.* 77:964-973, 2005, incorporated herein by reference) is used. Every spectrum is transformed into a PRM spectrum as described by Bandeira et al. (supra).

Bandeira et al. use a spectral similarity measure to decide whether two spectra come from the same peptide. While spectral similarity largely succeeds in identifying related spectra, in some cases it may erroneously pair nonrelated spectra. Although such false pairings are rare, they may cause problems if they connect two unrelated clusters. To remove false pairs, the heuristic approach from Ben-Dor et al. (*J. Comput. Biol.* 6:281-297, 1999 (incorporated by reference)) is used. This clustering procedure resulted in 567 clusters representing 98% of all unmodified and 96% of all modified peptides with three or more spectra in the original sample.

Each cluster of spectra is then collapsed into a single "consensus spectrum" that contains peaks present in at least k spectra in the cluster. The parameter k is chosen in such a way that the probability of seeing a peak in k spectra by chance is less than 0.01. The scores of matching peaks are summed up to score the peaks in the consensus spectrum.

variation of (i)). Two spectra form a "spectral pair" if their corresponding peptides are paired. Although the peptides that give rise to a spectral pair are not known in advance, the spectral pairs can be detected with high confidence using uninterpreted spectra.

For two spectra $S_1$ and $S_2$, the "spectral product" of $S_1$ and $S_2$ is the set of points $(x, y) \in \mathbb{R}^2$ for every $x \in S_1$ and $y \in S_2$ ($S_1$ and $S_2$ are represented as sets of masses). F*igure* 1*a* shows the spectral product for the theoretical spectra of two peptides, TEVMA (SEQ. ID. NO. 15) and TEVMAFR (SEQ. ID. NO. 16). The similarity between the two spectra is revealed by two diagonals (labeled "blue" and "red") in the spectral product.

Figure 2A:
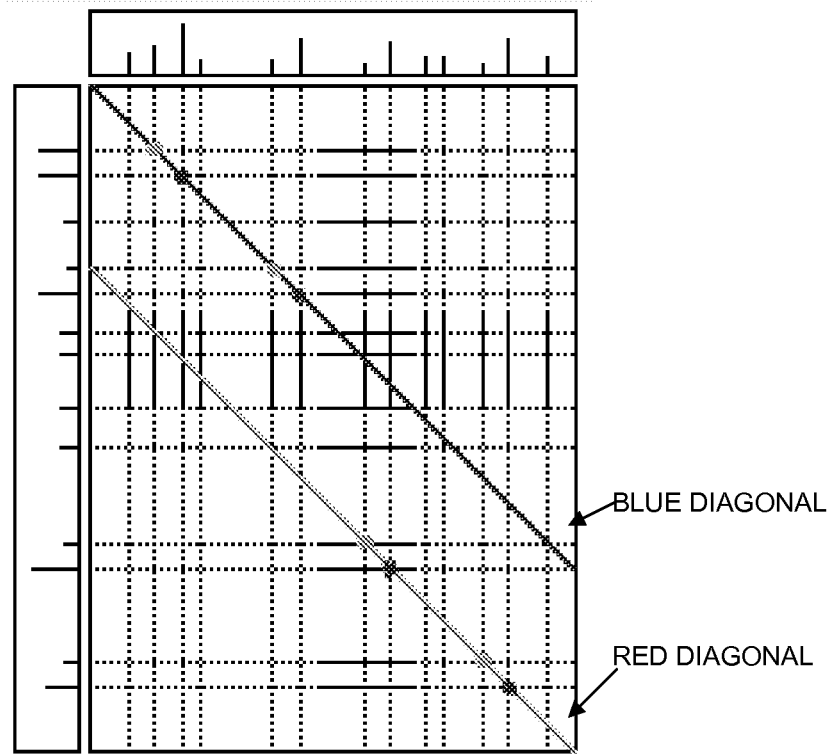
FIG. 2 illustrates the spectral product matrix for uninterpreted spectra with internal modification. The first spectrum corresponds to an unmodified peptide, and the second spectrum corresponds to a modified peptide.
Figure 2B:
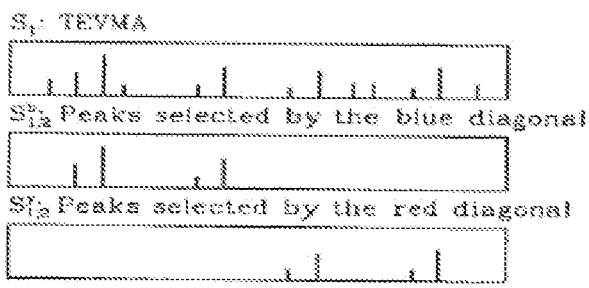
Figure 2B:
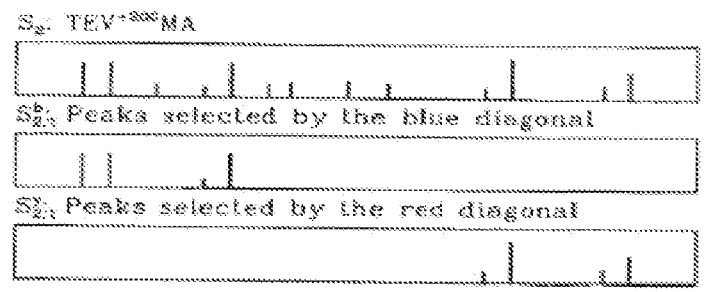

FIGS. 1*b* and 2 show pairs of uninterpreted spectra, denoted $S_1$ and $S_2$, and their spectral product. Although the "colors" of peaks are not known in this case, to distinguish between the two spectra one diagonal is referred to as "blue" and the other "red". One can use circles (matching peak masses) on the blue diagonal to transform the original spectrum $S_1$ into a new spectrum $S_{1,2}^b$ (FIG. 1*c*) with a much smaller number of peaks (a peak in $S_1$ is retained in $S_{1,2}^b$ only if it generates a circle on the blue diagonal). Similarly, one can transform $S_1$ into a spectrum $S_{1,2}^y$ using circles on the red diagonal. The peak scores in both spectra $S_{1,2}^b$ and $S_{1,2}^y$ are inherited from spectrum $S_1$. Similarly, the spectrum $S_2$ is transformed into $S_{2,1}^b$ and $S_{2,1}^y$.

Intuitively, if two spectra are unrelated, blue and red diagonals represent random matches and the number of circles appearing on these diagonals is small. Paired spectra, on the contrary, are expected to have many circles on these diagonals. Although this simple criterion (number of circles on two diagonals) would already allow one to roughly distinguish paired spectra from unrelated spectra, a more accurate test for finding spectral pairs is described below.

The "correlation score" of spectra $S_1$ and $S_2$ is defined as the total score of all peaks in $S_{1,2}^b$ and $S_{1,2}^y$: score $(S_1, S_2)$=score $(S_{1,2}^b)$+score $(S_{1,2}^y)$. In a similar way, score $(S_2, S_1)$=score $(S_{2,1}^b)$+$(S_{2,1}^y)$. $S_1$ and $S_2$ are accepted as a putative spectral pair if both the ratio

TABLE 1

| Type of spectra | | #Explained | | | #Unexplained | #Total | signal-to-noise ratio |
|---|---|---|---|---|---|---|---|
| | | b | y | Sarellite | | | |
| Single spectra (11760 spectra) | # peaks: | 9.48 | 9.26 | 20.07 | 35.25 | 74.05 | 0.27 |
| | % peaks: | 13% | 13% | 26% | 48% | | |
| | % score: | 28% | 28% | 19% | 25% | | |
| Consensus spectra (567 spectra) | # peaks: | 9.47 | 9.39 | 10.42 | 13.74 | 43.06 | 0.69 |
| | % peaks: | 22% | 22% | 24% | 82% | | |
| | % score: | 37% | 36% | 13% | 14% | | |
| Spectral pairs$_{i,j}^b$ (1569 pairs) | # peaks: | 6.47 | 0.2 | 0.38 | 1.69 | 8.64 | 3.83 |
| | % peaks: | 75% | 2% | 4% | 19% | | |
| | % score: | 87% | 2% | 4% | 7% | | |
| Star spectra (745 stars) | # peaks: | 8.38 | 0.52 | 0.92 | 2.9 | 12.72 | 2.89 |
| | % peaks: | 66% | 4% | 7% | 28% | | |
| | % score: | 88% | 3% | 2% | 7% | | |

As shown in Table 1, the resulting consensus spectra have unusually high signal to noise ratio (the number of unexplained peaks in the consensus spectra is reduced by a factor of 2.5). Some consistently co-occurring unexplained peaks were observed, possibly arising due to co-eluting peptides or unexplained fragment ions (e.g., internal ions). After clustering, there were 567 consensus spectra (that cover 93% of all individual spectra) and 862 unclustered spectra.

Peptides $P_1$ and $P_2$ form a "peptide pair" if either (i) $P_1$ differs from $P_2$ by a single modification/mutation, or (ii) $P_1$ is either a prefix or suffix of $P_2$ (which can be considered a $$\frac{\text{score}(S_1, S_2)}{\text{score}(S_1)} \text{ and } \frac{\text{score}(S_2, S_1)}{\text{score}(S_1)}$$

exceed a predefined threshold.

In addition to the correlation score test described above, a test is used to take into account the size of the MS/MS sample. The larger the set of spectra under consideration, the larger the chance that a certain correlation score can be achieved by chance. To account for this phenomenon, assume that the correlation scores between unrelated spectra approximately follow a Gaussian distribution. Thus, a correlation score is only considered significant if the probability of this score appearing by chance is below 0.01.

Figure 3A:
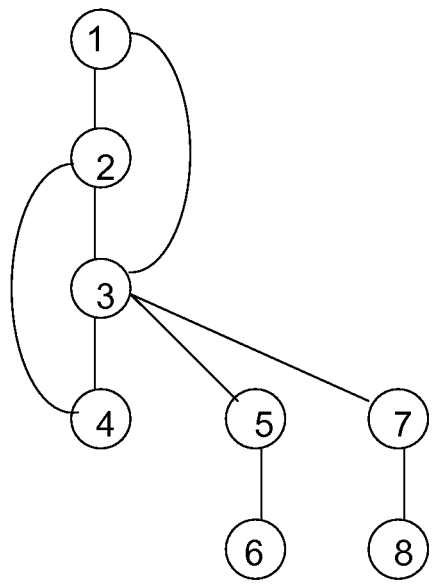
FIG. 3a illustrates a connected component of the spectral pairs graph for an IKKb protein sample.

The spectral pairs that satisfy both tests form the spectral pairs graph on the set of all spectra (FIG. 3). The spectral pairs graph for the IKKb dataset has 43 connected components with 1021 vertices and 1569 edges. The small number of connected components is not surprising since overlapping peptides in this dataset can be assembled into a small number of contigs (an effect previously explored by Bandiera et al. in the context of shotgun protein sequencing). The combined filtering efficiency of these criteria permitted retention of 78.4% of all correct spectral pairs at a precision level of 95% and identification of several different variants of most unmodified peptides. Table 1 describes the statistics of spectra $S_{i,j}$, including single spectra, consensus spectra, spectral pairs, and star spectra. Satellite peaks include fragment ions correlated with b and y peaks ($b-H_2O$, $b-NH_3$, a, $b^2$, etc.). Signal to noise ratio (SNR) is defined as the number of b ions over the number of unexplained peaks. Spectral pairs separate prefix and suffix ladders and make interpretation of resulting spectra $S_{i,j}^b$ relatively straightforward. Spectral stars (described below) further increase the number of b and y peaks in the resulting spectra. Note that b peaks are responsible for about 90% of the score in both paired and star spectra. The results are given only for the $S_{i,j}^b$ spectra since the $S_{i,j}^y$ spectra have the same statistics. The results show a dramatic increase in signal to noise ratio as compared to consensus spectra as well as individual spectra. Moreover, the spectral pairs provide nearly perfect separation between prefix and suffix ladders thus making follow up interpretation straightforward.

FIG. 1b illustrates case (ii) in the definition of spectral pairs. The situation becomes less transparent in case (i), namely, when modification/mutation occurs in the middle of peptide (FIG. 2). In this case, both detecting spectral pairs ($S_i$, $S_j$) and further processing them into spectra $S_{i,j}^b$ and $S_{i,j}^y$ is more complicated. A general algorithm is described below for deriving virtual spectra $S_{i,j}$ from spectral pairs that covers the case of internal modifications/mutations.

Let $S_1$ and $S_2$ be two spectra, and assume, without loss of generality, that $M(S_1) < M(S_2)$, where M(S) denotes the parent mass of S. Let $\Delta = M(S_2) - M(S_1)$. For simplicity, assume in the following that the masses in $S_1$ and $S_2$ are integers and that $S_i$ (i=1,2) contains the masses 0 and $M(S_i)$.

Denote by $M(S_1, S_2)$ the spectral product matrix of $S_1$ and $S_2$ and define a path in $M(S_1,S_2)$ to be a set of points in $\mathbb{R}^2$ that is composed of two diagonal segments $\{(x,x): a \leq x < b\}$ and $\{(x, x+\Delta): b < x \leq c\}$ for some $a \leq b \leq c$. Note that the first segment is on the blue diagonal and the second segment is on the red diagonal (one of the segments is empty when a=b or b=c). The endpoints of the path are the leftmost and rightmost points on the path.

The spectral alignment algorithm, described by Pevzner et al. (*J. Comput. Biol.* 7:777-787, 2000 (incorporated herein by reference)), finds the path from (0,0) to $(M(S_1), M(S_1)+\Delta)$ that contains the maximum number of points from $M(S_1,S_2)$. For the optimal path P, the projection of P onto $S_i$ (i.e., the set $\{x_1:(x_i, x_i-1) \in P\}$) gives a subset of $S_i$ which usually contains many b-ion peaks. However, this set can also contain many peaks corresponding to y and neutral loss ion peaks. In order to obtain better b-y separation, the spectral alignment problem is changed by selecting only a subset of the points in P: (1) Since the minimum mass of an amino acid is 57 Da, peaks are chosen with a distance of at least 57 between every two peaks, and (2) two points that are generated by a peak and its complement peak in $S_1$ or $S_2$ are not selected.

Formally, two peaks x and x' in a spectrum S are complements if $x+x'=M(S)+18$. A subset A of a spectrum S is called "antisymmetric" if it does not contain a complement pair. A set A is called "sparse" if $|x-x'| \geq 57$ for every x, x' ∈ A. Given a path P, a set $A \subseteq P$ is called "sparse" if the projection of A onto $S_1$ is sparse, and it is called "antisymmetric" if the projections of A onto $S_1$ and $S_2$ are antisymmetric (with respect to $S_1$ and $S_2$, respectively). The goal is to find the largest sparse antisymmetric subset of $M(S_1, S_2)$ that is contained in some path from (0,0) to $(M(S_1), M(S_1)+\Delta)$, and contains the points (0,0) and $(M(S_1), M(S_1)+\Delta)$.

The antisymmetric spectral alignment algorithm is described below. For simplicity of the presentation, a simple algorithm is described first, then several enhancements to the algorithm are described.

In a preprocessing stage, every element x of $S_1$ is removed if $x \notin S_2$ and $x+\Delta \notin S_2$. Denote $S_1=\{x_1, \ldots, x_n\}$ and $S_2=\{y_1, \ldots, y_m\}$, where $x_1 \geq 1 x_2 < \ldots < x_n$ and $y_1 < y_2 < \ldots < y_m$. Let N be the largest index such that $x_N \leq (M(S)+18)/2$.

A peak $x_i$ in $S_1$ will be called "left-critical" (resp., "right-critical") if $x_i+\Delta \in S_1$ (resp., $x_i-\Delta \in S_1$). Denote by $S_1^L$ and $S_1^R$ the left-critical and right-critical peaks in $S_1$, respectively.

For $i \leq n$, let Left(i) be the set of all sparse antisymmetric subsets of $S_1^L \cap [x_i-\Delta, x_i-57]$, and let Right(i) be the set of all sparse antisymmetric subsets of $S_1^R \cap [x_i+57, x_i+\Delta]$. Note that if $\Delta < 57$ then Left(i)=Right(i)=$\phi$ for all i, which simplifies the algorithm. In the following, assume that $\Delta \geq 57$.

For $i \leq N$ and $j > N$, define $D_1(i,j)$ to be the maximum size of a sparse antisymmetric set $A \subseteq M(S_1,S_2)$ such that 1. A is contained in the union of a path from (0,0) to $(x_i, x_i)$ and a path from $(x_j, x_j+\Delta)$ to $(M(S_1), M(S_1)+\Delta)$.
2. A contains the points (0,0), $(M(S_1), M(S_1)+\Delta)$, $(x_i, x_i)$ and $(x_j, x_j+\Delta)$.

If there is no set that satisfies the requirements above, $D_1(i,j)=0$.

Tables $D_2$ and $D_3$ are defined in a similar way: For $i \leq N < j$ and S ∈ Left(i), $D_2(i,j, S)$ is the maximum size of a sparse antisymmetric set $A \subseteq M(S_1, S_2)$ such that 1. A is contained in the union of a path from (0,0) to $(x_i, x_i+\Delta)$ and a path from $(x_j, x_j+\Delta)$ to $(M(S_1), M(S_1)+\Delta)$.
2. A contains the points (0,0), $(M(S_1), M(S_1)+\Delta)$, and $(x_j, x_j+\Delta)$. Moreover, if i>1 then A contains the point $(x_i, x_i+\Delta)$.
3. $\{x \in S_1^L: x_i-\Delta \leq x \leq x_i-57 \text{ and } (x, x+\Delta) \in A\}=S$.

For $i \leq N < j$ and S ∈ Right(j), $D_3(i,j, S)$ is the maximum size of a sparse antisymmetric set $A \subseteq M(S_1, S_2)$ such that:

1. A is contained in the union of a path from (0,0) to $(x_i, x_i)$ and a path from $(x_j, x_j)$ to $(M(S_1), M(S_1)+\Delta)$.
2. A contains the points (0,0), $(M(S_1), M(S_1)+\Delta)$, and $(x_i, x_i)$. If j<n, then A also contains the point $(x_j, x_j)$.
3. $\{x \in S_1^R: x_j+57 \leq x \leq x_j+\Delta \text{ and } (x, x) \in A\}=S$.

The following definitions apply: for $i \leq n$, prev(i)=i', where i' is the maximum index such that $x_{i'} \leq x_i-57$. If no such index exists then prev(i)=1. Similarly, next(i)=i', where i' is the minimum index such that $x_{i'} \geq x_i+57$. If no such index exists then next(i)=n. Define $$M_1^L(i, j) = \max_{i' \leq i} D_1(i', j)$$

$$M_1^R(i, j) = \max_{j' \geq j} D1(i, j')$$

$$M_2^R(i, j, S) = \max_{j' \geq j} D_2(i, j', S)$$

$$M_3^L(i, j, S) = \max_{i' \leq i} D_3(i', j, S)$$

Further, $$M_2^L(i, j, S) = \max_{i' \leq i} \max_{S'} D_2(i', j, S'),$$

where the second maximum is taken over all sets S' ∈ Left(i') that are consistent with S, namely S'∩[$x_i$–Δ, $x_i$–57]=S. Similarly, $$M_3^L(i, j, S) = \max_{j' \geq j} \max_{S'} D_3(i, j', S'),$$

where the second maximum is taken over all sets S' ∈ Right(j') such that S'∩[$x_j$+57, $x_j$+Δ]=S. One can now efficiently compute $D_1(i,j)$, $D_2(i,j, S)$, and $D_3(i,j, S)$ for all i, j, and S.

For computing $D_1(i,j)$, if either $x_i \in S_2$ or $x_j+\Delta \in S_2$, then by definition, $D_1(i, j)=0$. Also, $D_1(i,j)=0$ when $x_i$ and $x_j$ are complements, or when $x_j-x_i<57$. Furthermore, if i=1 and j=n then $D_1(i,j)=2$. Now, suppose that none of the cases above occurs. Then, $$D_1(i, j) = \begin{cases} M_1^L(prev(i), j) + 1 & \text{if } x_i > M(S_1 + 18 - x_j) \\ M_1^R(i, next(j)) + 1 & \text{otherwise} \end{cases}.$$

For computing $D_2(i,j, S)$, suppose that $x_i+\Delta$, $x_j+\Delta \in S_2$, $x_i$ and $x_j$ are not complements, and $x_j-x_i \geq 57$. If $x_j+\Delta$ is complement of $x_{j'}+\Delta$(with respect to $S_2$) for some i' ∈ {i,j} and j' ∈ S ∪ {j}, then $D_2(i,j, S)=0$. Otherwise, $$D_2(i, j, S) = \begin{cases} M_2^L(prev(i), j, S) + 1 & \text{if } x_i > M(S_1 + 18 - x_j) \\ M_2^R(i, next(j), S) + 1 & \text{otherwise} \end{cases}.$$

For computing $D_3(i, j, S)$, suppose that $x_i$, $x_j \in S2$, $x_i$ and $x_j$ are not complements, and $x_j-x_i \geq 57$. If $x_{i'}$ is complement of $x_{j'}$ (with respect to $S_2$) for some i' ∈ {i,j} and j' ∈ S ∪ {j}, then $D_3(i, j, S)=0$. Otherwise, $$D_3(i, j, S) = \begin{cases} M_3^L(prev(i), j, S) + 1 & \text{if } x_i > M(S_1 + 18 - x_j) \\ M_3^R(i, next(j), S) + 1 & \text{otherwise} \end{cases}.$$

The recurrence formula for computing $M_1^L$ is straightforward: For i=1, $M_1^L(i, j)=D_1(i, j)$, and for i>1, $M_1^L(i, j)=\max\{D_1(i, j), M_1^L(i-1, j)\}$. The recurrence of $M_1^R$, $M_2^R$ and and $M_3^L$ are similar.

$$M_2^L(i, j, S) = \max\left\{D_2(i, j, S), \max_{S'} M_2^L(i-1, j, S')\right\},$$

where the second maximum is taken over all sets S' ∈ Left(i–1) that are consistent with S. The computation of $M_3^R(i, j, S)$ is similar.

After filling the tables $D_1$, $D_2$, and $D_3$, the size of the optimal set of points can be determined by taking the maximum value in these tables. The corresponding optimal set can be found by traversing the dynamic programming tables starting from the cell containing the maximum value.

Using additional data structures, each cell of $D_1$, $D_2$, and $D_3$ can be computed in constant time. Thus, the time complexity of the algorithm is $O(kn^2)$, where k= max{|Left(1), ..., Left(N), Right(N+1), ..., Right(n)|}. Although k can be exponential in n, in practice, k has small values.

The preceding algorithm is similar to the algorithm of Chen et al. (J. Comput. Biol. 8:325-337, 2001) for de novo peptide sequencing. However, unlike de novo peptide sequencing, the problem is two-dimensional, which adds complexity to the algorithm. Dynamic programming is used to compute optimal sets of points that are contained in two paths, one path starting at (0,0) and the other path starting at $(M(S_1), M(S_1)+\Delta)$. By keeping two paths, for each set of points built, the projection on $S_1$ is antisymmetric. In order to keep the projection on $S_2$ antisymmetric, additional information is needed, which is kept in a third dimension of the dynamic programming table.

A set of spectra incident to a spectrum $S_1$ in the spectral pairs graph is called a "spectral star". For example, the spectral star for the spectrum derived from peptide 3 in FIG. 3 consists of multiple spectra from 5 different peptides. Even for a single spectral pair $(S_1, S_2)$, the spectra $S_{1,2}^b$ and $S_{1,2}^y$ already have high signal to noise ratio and rich prefix and suffix ladders. Spectral stars allow further enrichment of the prefix and suffix ladders (see Table 1). A spectral star consisting of spectral pairs $(S_1, S_2), (S_1, S_3), \ldots, (S_1, S_n)$ increases the signal to noise ratio by considering 2(n–1) spectra $S_{1,i}^b$ and $S_{1,i}^y$ for $2 \leq i \leq n$. These spectra are combined into a star spectrum $S_1^*$ using the previously-described clustering approach. This needs to be done with caution since spectra $S_{1,i}^b$ and $S_{1,i}^y$ represent separate prefix and suffix ladders. Therefore, one of these ladders needs to be reversed to avoid mixing prefix and suffix ladders in the star spectrum. The challenge is that the assignments of upper indexes to spectra $S_{1,i}^b$ and $S_{1,i}^y$ are arbitrary and it is not known in advance which of these spectra represents b ions and which represents y ions (i.e., it may be that $S_{1,i}^b$ represents the suffix ladder while $S_{1,i}^y$ represents the prefix ladder).

For spectral stars, a simple greedy approach to the binary flip-cut (BFC) problem described by Dancik, et al. (J. Comput. Biol. 4:119-126, 1997 (incorporated herein by reference)) may be used. Using this approach, one can arbitrarily select one of the spectra $S_{1,i}^b$ and $S_{1,i}^y$ and denote it $S_{1,i}$. $S_{1,2}$ is selected as an initial consensus spectrum. For every other spectrum $S_{1,i}$ ($2 \leq i \leq n$), it must be determined whether $S_{1,i}$ or its reversed copy $S_{1,i}^{rev}$ better fits the consensus spectrum. In the former case, $S_{1,i}$ is added to the growing consensus, while in the latter case $S_{1,i}^{rev}$ is added.

After the greedy solution of the BFC problem, all orientations of all spectra in the spectral star are known. The final step in constructing star spectrum S* from the resulting collection of $S_{1,i}$ spectra uses the consensus spectrum approach described above. Table 1 shows the power of spectral stars in further enriching the prefix/suffix ladders.

Figure 4:
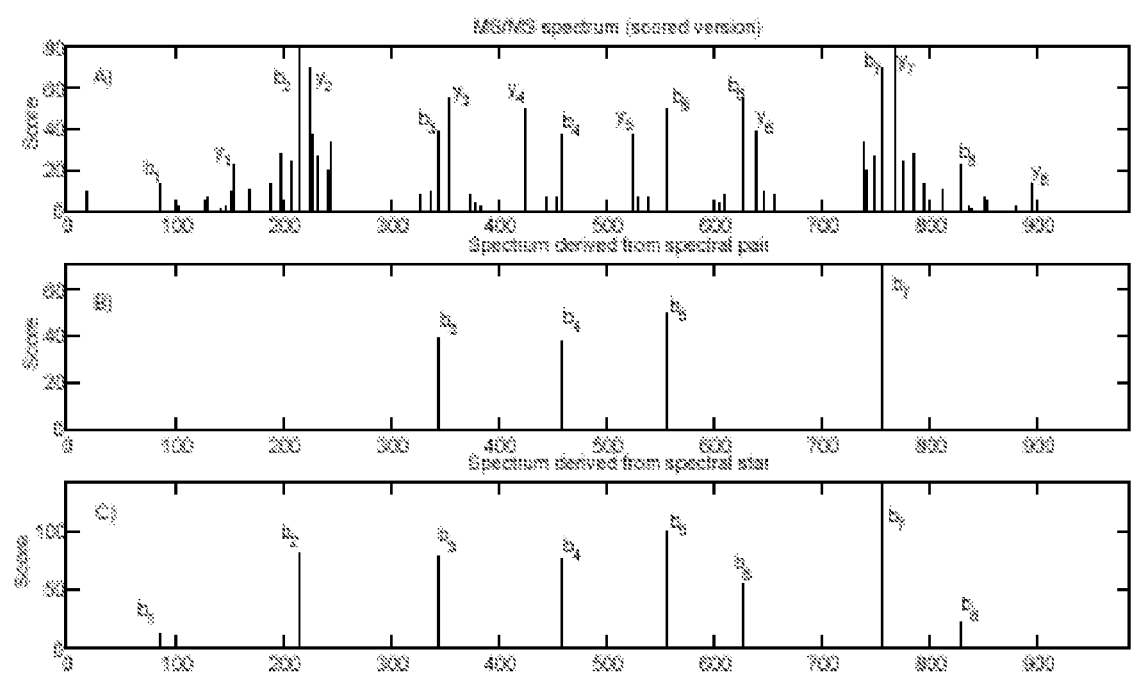
FIG. 4 shows plots of spectra processed according to the inventive method, illustrating improvements in signal to noise ratio.

An example of the improvement in signal to noise ratio that can be achieved using the present method is illustrated in FIG. 4. The scored MS/MS spectrum for peptide SEELVAEAH (SEQ. ID NO. 26) has both prefix and suffix peaks along with several noise peaks (upper spectrum). Using the spectral product of a pair of spectra, many of the noise and suffix peaks that do not reside on the selected diagonal are eliminated. Though paired spectra provide very good separation of prefix/suffix ladders they may sometimes be too selective (e.g., causing the loss of the $b_1$, $b_2$, $b_6$, $b_8$ peaks) (middle spectrum). By incorporating more paired spectra to form a spectral star, all noise peaks are removed and all missing prefix peaks are adequately recovered, as shown in the lower spectrum of FIG. 4.

The high quality of the spectra derived from spectral pairs ($S_{i,j}$) and spectral stars ($S_i^*$) makes de novo interpretation of these spectra relatively straightforward. Since these spectra feature excellent separation of prefix and suffix ladders and a small number of noise peaks, de novo reconstructions of these spectra produce reliable (gapped) sequences that usually contain long correct tags. The standard longest path algorithm is used to find the highest scoring path, and a set of suboptimal paths, in the spectrum graph of spectra $S_{i,j}$ and $S_1^*$. In contrast to the standard de novo algorithm, it is not necessary to reconstructing the entire peptide, and the found path can be shortened by removing its prefix/suffix if it does not explain any peaks. As a result, the found path does not necessarily start or end at the beginning or end of the peptide. Also, antisymmetric path construction is not invoked since the spectra $S_{i,j}$ and $S_i^*$ already separate prefix and suffix ladders.

On average, de novo reconstructions of the consensus spectra correctly identify 72% of all possible "cuts" in a peptide (i.e., on average, $0.72 \cdot (n-1)$ b ions (y ions) in a peptide of length n are explained). This is a very high number since the first (e.g., $b_1$) and the last (e.g., $b_n-1$) b ions are rarely present in the MS/MS spectra, thus making it nearly impossible to explain more than 80% of "cuts" in the IKKb sample. Moreover, on average, the explained b peaks account for 95% of the total score of the de novo reconstruction implying that unexplained peaks usually have very low scores. In addition to the optimal de novo reconstruction, suboptimal reconstructions and long peptide tags are generated.

Benchmarking in mass spectrometry is inherently difficult due to the shortage of manually validated large MS/MS samples that represent "golden standards". While the ISB dataset represents such a golden standard for unmodified peptides, large validated samples of spectra from modified peptides are not currently available. As a compromise, the inventive algorithm was benchmarked using a set of 11,760 spectra from the IKKb dataset that were annotated by InsPecT (with p-values$\leq$0.05) with comparisons against SEQUEST, Mascot and X!Tandem. The entire analysis (starting from clustering and ending with interpretations) of the IKKb dataset took 32 minutes on a standard desktop processor, well below the expected running time of searching the same dataset against even a medium sized database.

The following results were obtained for both spectral pairs and spectral stars:

InsPecT identified 515 unmodified peptides in the IKKb sample, 413 of which have some other prefix/suffix or modified variant in the sample and are thus amenable to pairing. Spectral pairs were found for 386 out of these 413 peptides. Moreover, 339 out of these 386 peptides had spectral pairs coming from two (or more) different peptides, i.e., pairs ($S_1$, $S_2$) and ($S_1$, $S_3$) such that spectra $S_2$ and $S_3$ come from different peptides.

The average number of (gapped) de novo reconstruction (explaining at least 85% of optimal score) for spectral stars was 10.4. While the spectral stars generate a small number of gapped reconstructions, these gapped sequences are not well suited for fast membership queries in the database. Therefore, every gapped de novo reconstruction was transformed into an ungapped reconstruction by substituting every gap with all possible combinations of amino acids. On average, this results in 165 sequences of length 9.5 per spectrum. For 86% of peptides, one of these tags is correct.

While checking the membership queries for 165 sequences can be done rapidly with database indexing (at most, one of these sequences is expected to be present in the database), there is no particular advantage in using such superlong tags (9.5 amino acids on average) for a standard database search. (Note that the actual number of queries is twice as large since every "reversed" sequence must also be checked. This can be avoided by accounting or reverse variants during the database indexing step.) A tag of length 6-7 will also typically have an unique hit in the database. However, the long 9-10 amino acid tags have distinct advantages in difficult nonstandard database searches, e.g., discovery of new alternatively spliced variants or fusion genes via MS/MS analysis. Moreover, for a standard search one can generate the smaller set of shorter (67 amino acids) tags based on the original gapped reconstruction and use them for membership queries. The obtained gapped reconstruction was used to generate such short 6 aa tags (each such tag was allowed to have at most one missing peak). All possible continuous l-mers were enumerated by substituting every gap with all possible combinations of amino acids. (It may be necessary to limit the number of reconstructions to 100 if the number of continuous sequences becomes too large.) On average, each consensus spectrum generates about 50 6-mer tags. The results showed that 82% of spectra derived from spectral stars contain at least one correct 6-mer tag.

Figure 5A:
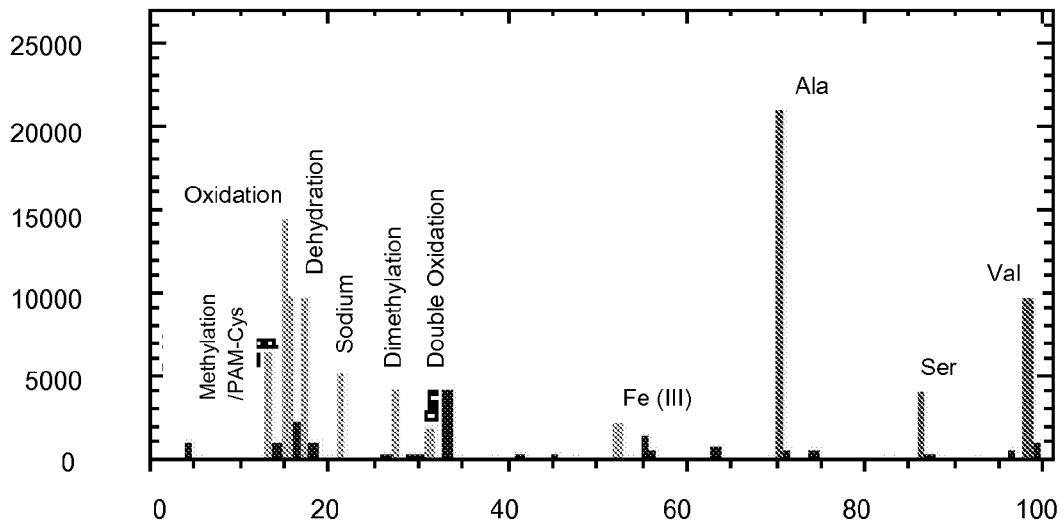
FIG. 5a is a histogram of absolute parent mass differences for all detected spectral pairs.

The inventive method provides for detection of modifications without any reference to a database. The difference in parent masses within a spectral pair either corresponds to a modification offset (case (i) above) or to a sum of amino acid masses (case (ii)). Therefore, the modification offsets present in the sample can be revealed by the parent mass differences within spectral pairs while their positions and specificities can be determined from de novo reconstructions. While not every difference in parent mass corresponds to a post-translational modification (PTM) offset (some spectral pairs may be artifacts), the histogram of parent mass differences (FIG. 5) reveals the PTMs present in the IKKb sample. FIG. 5a is a histogram of absolute parent mass differences for all detected spectral pairs. The y-axis represents the number of spectral pairs with a given difference in parent mass. For clarity, mass range 1-100 is shown. The peaks at masses 71, 87, and 99 correspond to amino acid masses, and the peaks at masses 14, 16, 18, 22, 28, 32, and 53 correspond to known modifications. The peak at mass 34 corresponds to a modification that remains unexplained to date. Indeed, 7 out of 8 most frequent parent mass differences in FIG. 5 are confirmed by Tsur et al. (*Nat. Biotechnol.*, 23:1562-1567, 2005) via a database search as being among 8 most common PTMs in IKKb.

EXAMPLES

Dataset 1: The human inhibitor of nuclear factor kappa B kinase beta (IKKb) dataset is a set of MS/MS spectra collected from multiple IKKb samples. Each sample was separately digested with multiple proteases (trypsin, elastase, Glu-C) resulting in an overall rich pattern of spectra from overlapping peptides. IKK is known to be a key signaling complex involved in controlling cell proliferation, survival, anti-apoptosis, and tumorigenesis and its relationships to insulin resistance were the subject of recent intensive studies. The IKKb dataset contains 6126 reliably identified spectra from 524 unmodified peptides and 1383 reliably identified spectra from 346 modified peptides, out of a total of 45,500 MS/MS spectra. (The IKKb dataset has been extensively analyzed using SEQUEST, Mascot, X!Tandem, and InsPecT, resulting in many reliably identified and validated peptides and thus constitutes a gold standard against which to benchmark the performance of the inventive sequencing approach.) The IKKb dataset also contains an unusually high percentage of modified peptides—40% of all identified peptides were modified one or more times. The high number of spectra from modified peptides makes this a challenging dataset in a sequencing context and provided a good test of the inventive algorithm's ability to integrate spectra of modified peptides in the assembly of proteins sequences.

Dataset 2: The second dataset is a set of MS/MS spectra from a sample of *crotalus atrox* venom proteins. This venom was chosen for benchmarking the inventive approach because it is relatively well studied and several of its proteins, ranging from 5-70 kDa, have been previously sequenced.

Briefly, the sample was reduced with DTT cysteines alkylated with iodoacetamide. The proteins that had not already precipitated were further precipitated with 60% ice-cold ethanol. After centrifugation, the supernatant was removed and discarded. The pellet was washed several times with 95% cold ethanol, then re-suspended in 0.1% Rapigest (acid-labile SDS-like detergent). Four aliquots were created and diluted for 2 hour digestions at pH 8.0 in 100 mM $NH_4HCO_3$; trypsin and Lys-C digest performed in 0.085% Rapigest; chymotrypsin and Asp-N digest was performed in 0.01% Rapigest. Digestions were terminated and detergent cleaved by acidifying with trifluoroacetic acid (TFA) pH 2. LC/MS/MS data was collected using a 2 hour reversed-phase gradient on a 75 uM I.D Magic C-18 column with data dependent MS/MS on a Thermo® LTQ. MS/MS peak lists were extracted from the RAW files using SpectrumMill in centroid mode. A database of 5510 venom proteins was obtained from SwissPROT (3 Aug. 2006) by selecting all proteins from the taxa Serpentes, including 33 proteins and fragments from *Crotalus Atrox*. This database was extended with 19 protein sequences from common contaminants and proteases and 5529 "decoy" shuffled versions of all protein sequences. MS/MS spectra were searched against the database using InsPecT with a peptide mass tolerance of 2.5 Da and fragment peak tolerance of 0.5 Da. The "decoy" database was used to select a false discovery rate of 5% and all retained peptides had an InsPecT-assigned p-value of 0.05 or less. Proteins were identified by iteratively selecting the protein sequence that explained the largest number of identified spectra (minimum 10 spectra per protein).

Several pre-processing steps were applied to the spectra, including parent mass correction, parent charge estimation and clustering of multiple spectra from the same peptide as described in above. In addition, every peak was replaced with its likelihood score, as described by Frank et al. (*Analytical Chem.* 77:964-973, 2005, incorporated herein by reference.) This scoring combines each peak's intensity, b-y complementarity and presence/absence of neutral losses into a single likelihood score. It has the additional effect of making every spectrum symmetric—a desirable transformation since it is difficult to tell ab initio which peaks come from prefix fragments (e.g., b-ions) and which come from suffix fragments (e.g., y-ions).

The purpose of the spectral alignment described above is to find pairs of spectra from overlapping peptides (spectral pairs). Conceptually, this procedure is akin to aligning inter-bead distances in a beaded necklace in order to detect overlaps between MS/MS spectra without knowing the corresponding peptides.

The algorithm for detection of spectra from overlapping peptides follows the inventive approach described herein. Spectral alignment translates the powerful Smith-Waterman sequence alignment technique (Smith and Waterman, *J. Mol. Biol.*, pp. 195-197, 1981) to the realm of MS/MS analysis. Similar to the dynamic programming matrix in sequence alignment, a spectral matrix is constructed in which an optimal path is identified. Intuitively, the spectral matrix of spectra S and S', is the set of pairs of peaks (p ∈ S, p' ∈ S'), called "matching peaks" (FIG. 6). Pairs of matching peaks may be connected by jumps as described below and shown in FIG. 6, with oblique jumps corresponding to putative modifications.

Figure 6A:
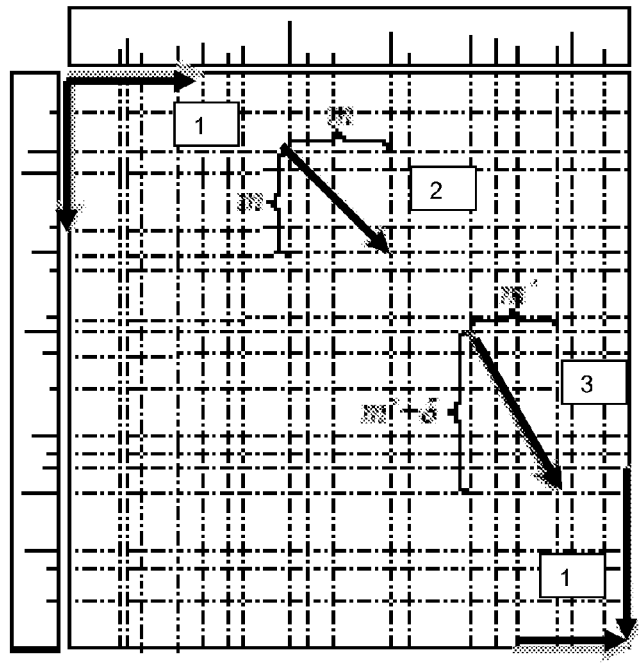
FIG. 6 illustrates a spectral matrix (FIG. 6a) and the possible types of spectral alignment: prefix/suffix alignment (6b); modified/unmodified alignment (6c) and partial-overlap alignment (6d).
Figure 6B:
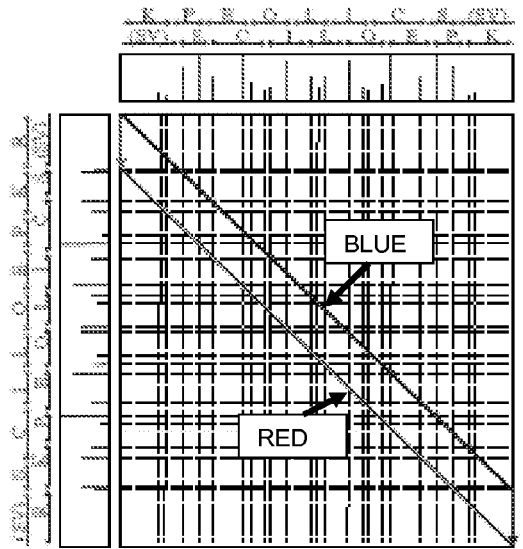
Figure 6C:
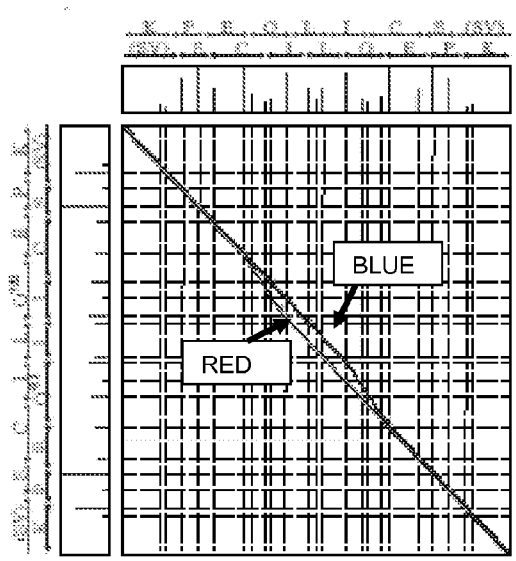
Figure 6D:
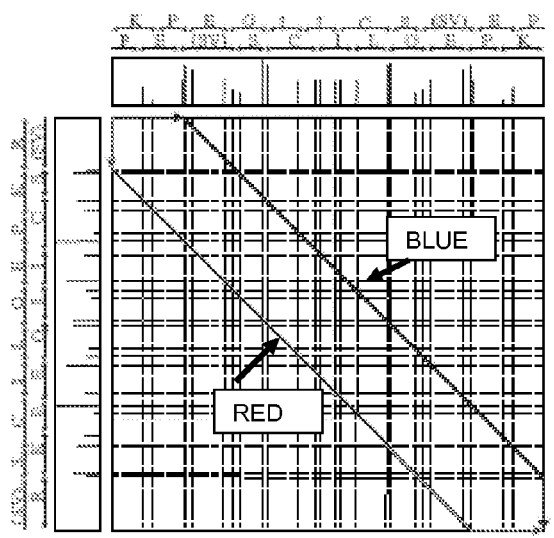
Figure 7A:
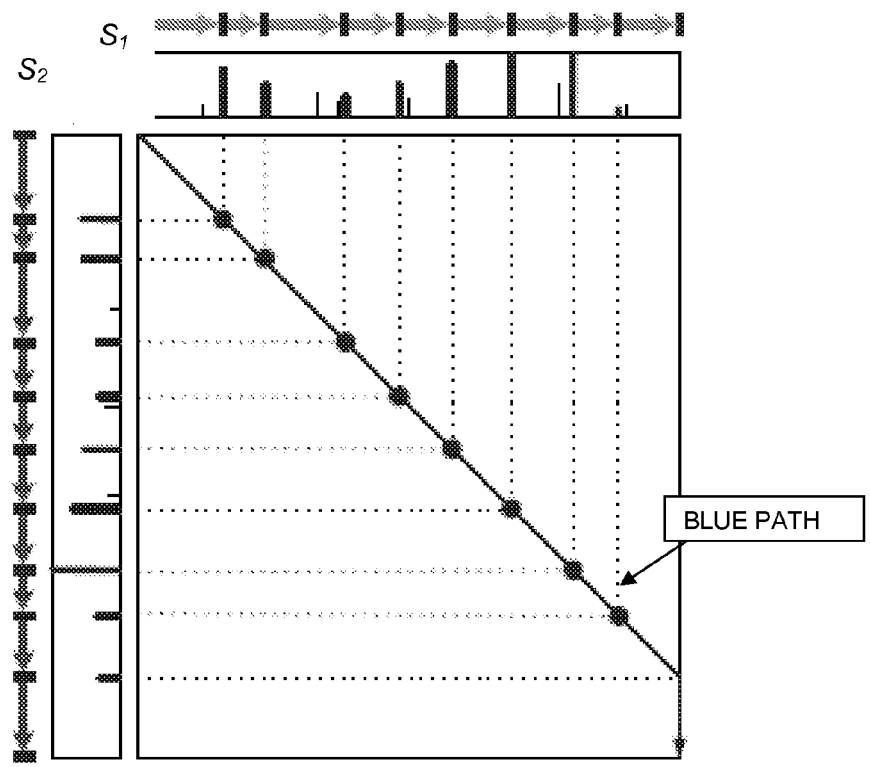
FIG. 7 shows a spectral alignment between spectra $S_1$ and $S_2$ (FIG. 7a); the glue spectrum peaks matched by spectral alignment and the resulting graph after gluing all matching peaks (FIGS. 7b and 7c); and an $\mathcal{A}$-Bruijn graph after replacing parallel edges with edge multiplicity (FIG. 7d).
Figure 7B:
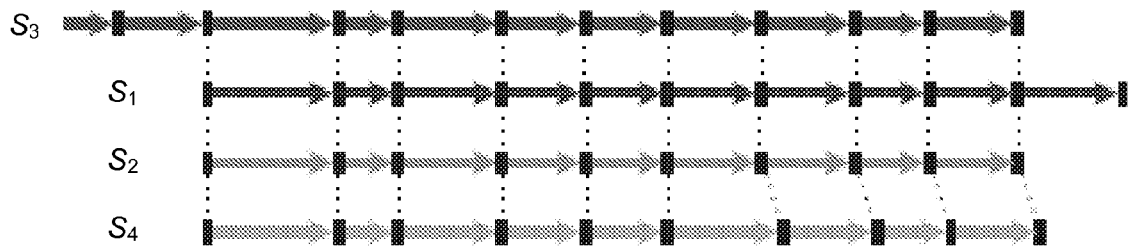
Figure 7C:
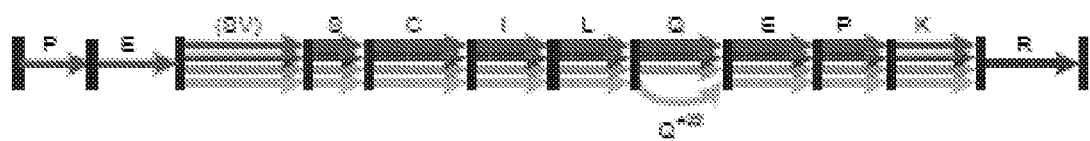
Figure 7D:
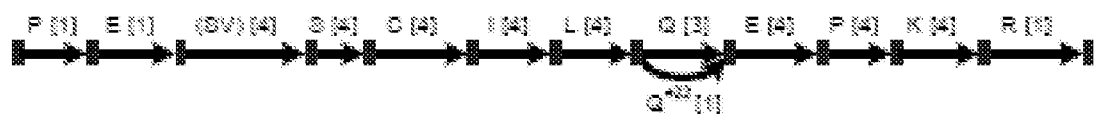

The alignment of two spectra is defined on the set of all matching peaks—each pair of matching peaks is represented as an intersection of vertical and horizontal dotted lines on the spectral matrix (FIG. 6a). 18 peaks in the first spectrum and 17 peaks in the second spectrum result in 17×18 matching peaks in the spectral matrix. Matching peaks may be connected by three types of jumps: horizontal/vertical; diagonal and oblique. A spectral alignment is defined as a sequence of jumps from the top-left corner to the bottom-right corner of FIG. 6a. Spectral alignments can be considered with any number of diagonal jumps but a limited number of other jumps. There are three types of spectral alignments: 1) prefix/suffix alignments use a single horizontal/vertical jump (either at the top-left or bottom-right) (FIG. 6b); 2) modified/unmodified alignments use a single oblique jump (FIGS. 6c); and 3) partial-overlap alignments use one horizontal/vertical jump at the top-left corner and another at the bottom-right corner (FIG. 6d). The optimal alignment of two spectra is an alignment with the longest sequence of valid jumps on the spectral matrix. The alignment of b-ions is shown as "blue" and y-ions as "red". Since MS/MS spectra commonly lack peaks in the low/high mass regions, horizontal/vertical jumps can be accepted where no peaks are matched.

Similar to classical sequence alignment, the optimal path (i.e., sequence of jumps) in the spectral matrix reveals the relationships between spectra. If spectra S and S' originate from overlapping peptides then there exists a path in this graph containing a large number of matching peaks, otherwise spectra S and S' are likely to be unrelated. Algorithmically, spectral alignment is more complex than sequence alignment since in the former case one optimizes two correlated paths in the spectral matrix (one corresponding to b-ions and another corresponding to y-ions) while in the latter case, one is only concerned with a single path.

FIG. 6 presents three cases where spectral alignments help reveal overlapping and modified peptides from the IKKb dataset without attempting to interpret the spectra: FIG. 6b: SVSCILQEPK (SEQ. ID. NO. 20) and SVSCILQEPKR (SEQ. ID. NO. 24) (suffix extension); FIG. 6c: SVSCILQEPK (SEQ. ID. NO. 20) and SVSCILQ (SEQ. ID NO. 22)+22EPK (SEQ. ID NO. 23) (modified variant); and FIG. 6d: PESVSCILQEPK (SEQ. ID. NO. 21) and SVSCILQEPKR (SEQ. ID. NO. 24) (partial-overlap). The corresponding optimal paths (shown as the "blue diagonal" for b-ions and "red diagonal" for y-ions) and selected matching peaks between the different spectral pairs are illustrated in FIG. 6. Note that choosing where to place the jumps implicitly defines the type of spectral pair: modified/ unmodified pair if there is an oblique jump in the middle; prefix/suffix pair if there is a single horizontal/vertical jump at the end/start; or overlap pair if there is one horizontal/vertical jump at the start and another at the end. The spectral alignment places the jump(s) in a position that maximizes the total scores of all matching peaks.

As a final step in the spectral alignment stage, one can capitalize on a by-product of spectral alignment—the separation of b- and y-ions in the aligned spectra. Although the colors of the paths are unknown to the algorithm it turns out that, with high probability, the "blue" and "red" paths cleanly separate b and y-ions. This separation is used to transform every aligned spectrum S into a star spectrum, which is a subset of S composed of mostly b-ions or mostly y-ions, but not both. Star spectra were shown above to contain very few noise peaks while retaining most b-ions (or y-ions) and to be extremely selective of same-type ions (i.e., only b or only y).

Combining pairwise spectral alignments into a single multiple alignment reveals peaks that are simultaneously supported by all or most of the aligned spectra.

Note that while a spectral alignment is able to identify the mass and location of a modification, it is not immediately obvious which spectrum comes from the modified peptide, i.e., whether the modification corresponds to a loss or gain of residue mass. The situation becomes more complex in the case of multiple modifications on the same peptide. The same reasons help explain why assembly of de novo interpretations from the aligned spectra would lead to limited success at best. Even when no modifications are present, accurate de novo sequencing of MS/MS spectra is a difficult problem, often resulting in several possible peptides that explain the spectrum almost equally well. Thus, while committing any spectrum to a particular peptide would ignore the multiple alignment, considering all possible combinations of all top peptide interpretations would quickly lead to a combinatorial explosion of assembly configurations. However, the set all possible interpretations of any given spectrum can be represented in a compact way by a spectrum graph in which each peak in the spectrum defines a vertex and two vertices are connected by an edge if their peak masses differ by one or two amino acid masses. Also, each vertex is assigned a score equal to the intensity of the corresponding spectrum peak. In this representation, every possible peptide interpretation corresponds to a path from zero to the spectrum's parent mass.

FIG. 2a illustrates two simplified spectrum graphs for the aligned spectra $S_1/S_2$, showing only the vertices for the true b-ions ("blue") and edges for the correct peptide path (along the y-axis for $S_1$ and x-axis for $S_2$).

In the terms of the bead necklace analogy, each of these peptide paths would correspond to a necklace fragment from one of the original necklaces. Thus, one would seek to reconstruct the original sequence of beads by finding similar pairs of overlapping fragments and "gluing" the matching beads to form a long chain identical to the original necklace model. FIG. 7 illustrates how this intuitive notion can be applied in the realm of spectral assembly: use spectral alignment to find the set of matching peaks between $S_1/S_2$ (FIG. 6b) and use these matches to glue the corresponding spectrum graph vertices (FIG. 6c). When applied to the simplified spectrum graphs in FIG. 7a, this would result in a merged spectrum graph with a single peptide path spelling the consensus sequence of $S_1$ and $S_2$. These merged spectrum graphs will be referred to as "$\mathcal{A}$-Bruijn graphs".

$\mathcal{A}$-Bruijn graphs were first proposed by Pevzner et al. (*Genome Res.* 14:1786-1796, 2004) in the context of repeat analysis and DNA fragment assembly. In this approach, every DNA read is represented as a path through nucleotides. All paths (reads) are "glued" using matching nucleotides as pairwise gluing instructions. However, while each DNA read defines a single path through its nucleotide sequence, any given spectrum will correspond to a spectrum graph encoding many possible paths through its peaks. In fact, if genomic sequences did not contain so many similar and long repetitive regions, they would be easier to assemble than protein sequences from MS/MS spectra.

The process of using matching peaks to glue spectrum graphs into a single $\mathcal{A}$-Bruijn graph is illustrated in FIG. 7. Note that edges between glued vertices are also glued if originally labeled with the same amino acid. Formally, an $\mathcal{A}$-Bruijn graph is constructed as follows: given a spectral alignment S(S, S') on two spectra S and S' and two corresponding spectrum graphs G and G', output a single $\mathcal{A}$-Bruijn graph $\mathcal{G}$ having G and G' as subgraphs. The specific gluing procedure is defined by the following operations:

1. Vertices in $\mathcal{G}$; vertices $v_i \in G$ and $v'_j \in G'$ are glued into a single vertex in $\mathcal{G}$ if the corresponding peaks $p_i \in S$ and $p'_j \in S'$ are matched in S(S, S'). All remaining non-matched vertices are imported directly into $\mathcal{G}$. Each $\mathcal{A}$-Bruijn vertex is scored by the sum of its grouped peaks' intensities.

2. Edges in $\mathcal{G}$; all edges in G and G' are imported directly into $\mathcal{G}$. However, edges are also glued if the endpoint vertices in G are glued to the endpoint vertices in G' and the edges are labeled with the same mass. Such pairs of edges, say e and e', are replaced by a single edge e" of the same mass.

Figure 8:
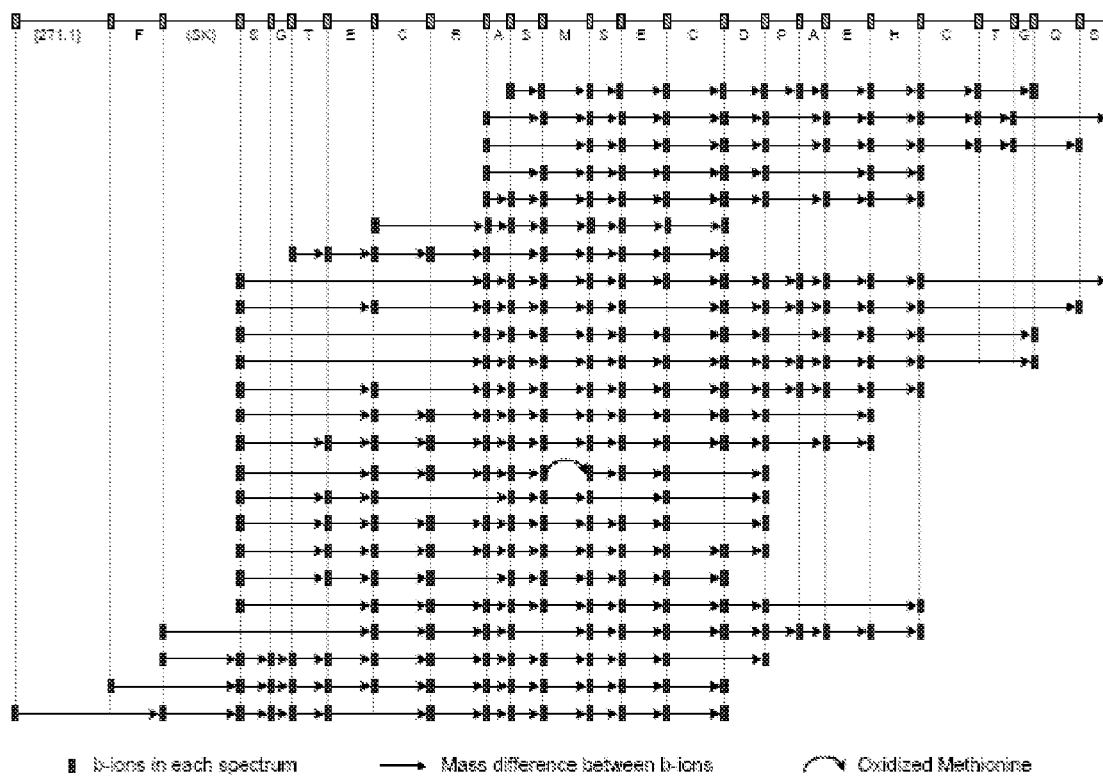
FIG. 8 illustrates a contig assembling 24 spectra covering a 25 amino acid portion of *Crotalus Atrox* Catracollastatin, where the top line shows the de novo contig sequence reconstructed from the assembled spectra and the remainder shows the MS/MS spectra assembled in the contig, where each line corresponds to a different spectrum.

The construction of an $\mathcal{A}$-Bruijn graph for a set of spectra and a set of spectral alignments is a straightforward iteration of the gluing operations described above. An example of a long sequence covering a 25 amino acid portion of *Crotalus Atrox*Catracollastatin (SEQ. ID. NO. 25) obtained from a set of 24 assembled spectra is illustrated in FIG. 8, where the top line shows the de novo contig sequence reconstructed from the assembled spectra. The remaining lines show the MS/MS spectra assembled in the contig, where each line corresponds to a different spectrum where matched b-ions are shown as rectangles connected by arrows.

However, errors in the spectral alignments may lead to the incorrect gluing of some peaks and generate inconsistent vertices in the $\mathcal{A}$-Bruijn graph. In particular, it sometimes happens that multiple peaks from the same spectrum end up glued in the same vertex. Fortunately, these inconsistencies are easily detected and the following techniques can be used to resolve them:

Briefly, the composite vertex splitting procedure is as follows: find the highest scoring edge e connecting a composite vertex $v^c$ to a non-composite vertex v. Then, split the set of peaks in $v^c$ into two disjoint sets of peaks $v^c$ and $v_e^c$ such that $p \in v_e^c$ if e is incident on p or $p \in v^c$ otherwise. Since $v_e^c$ is guaranteed to be non-composite (only one peak per spectrum can match the mass difference in e) these steps are repeated until no composite vertex remains.

Generally, finding the heaviest path in the $\mathcal{A}$-Bruijn graphs is a straightforward procedure because these graphs are usually acyclic. In such cases, a simple dynamic programming algorithm solves the problem efficiently. In short, each vertex v keeps track of the score ps(v) of the highest scoring path reaching it. Then, for every source $v_s$ and every edge $e=(v_s, v)$, update ps(v) to max(ps(v), ps($v_s$)+score(e)) and remove e from the graph. After all edges have been processed, locate the vertex with the highest score and trace back the highest scoring path. There are, however, some cases where the $\mathcal{A}$-Bruijn graph contains cycles due to an incorrect alignment of one or more spectra. While, in general, finding the heaviest path in a graph with cycles is a difficult problem, a small change to the standard algorithm performs well for $\mathcal{A}$-Bruijn graphs generated from spectral alignments. Essentially, a cycle in the $\mathcal{A}$-Bruijn graph would cause the algorithm to fail because at some point there would still be unprocessed vertices in the graph but no more sources to iterate over (cycles contain no source vertices). In this situation, the vertex in the graph with the lowest percentage of unprocessed incoming edges was located and converted into a source by removing all such edges from the graph.

After an $\mathcal{A}$-Bruijn graph is constructed, the consensus sequence is defined as the heaviest path in the resulting directed graph. On most occasions, the resulting $\mathcal{A}$-Bruijn graph is a directed acyclic graph and thus standard algorithms are readily available to solve this problem. On the rare occasions when incorrect spectral alignments induce directed cycles in the $\mathcal{A}$-Bruijn graph, a simple greedy modification to the standard heaviest path algorithm works well on the $\mathcal{A}$-Bruijn graphs.

TABLE 2

|  | IKKb | venom |
|---|---|---|
| Number of contig: | 104 | 194 |
| Spectrum coverage‡ | 57% | 54% |
| Contig coverage§ | 87% | 75% |
| Sequencing coverage† | 85% | 96% |
| Average counts per contig: | | |
| # assembled spectra | 11.4 | 15.1 |
| # assembled peptides | 6.5 | 7.3 |
| De novo sequencing: | | |
| a) matched the database | 87 (84%) | 141 (73%) |
| b) matched a homologeus peptide | 2 (2%) | 28 (14%) |
| c.1) suggesis a new peptide | 0 | 6 (3%) |
| c.2) from unidentified contig | 11 (11%) | 12 (6%) |
| d) Incorrect | 4 (4%) | 7 (4%) |

| IKKb dataset | Sequencing coverage† | Sequencing accuracy¶ |
|---|---|---|
| IKKb | 82% | 92% |
| Overall (12 proteins) | 88% | 82% |
| Venom dataset | | |
| Catrocollastailn (Q90288) | 87% | 90% |
| Hemorrhagic metalloproteinase (P34182) | 90% | 87% |
| Vascular apoptosis-inducing protein 1 (Q9DGB9) | 100% | 99% |
| Phospholipase A2 homolog Cax-K49 (QSUVZ7) | 100% | 92% |
| Phospholipase A2 precursor (Q98391) | 92% | 94% |
| Overall (14+ proteins)◊ | 95% | 90% |

Table 2 lists the number of contigs assembled from each dataset (IKKb and venom) along with some statistics on $\mathcal{A}$-Bruijn graph construction and sequencing; de novo sequences obtained from the contigs are referred to as contig sequences. Overall, these contig sequences covered 96% of all assembled regions in the venom dataset and 85% in the IKKb dataset. Table 2 also shows the sequencing accuracy and coverage for the most abundant proteins in each dataset.

It may appear that sequencing proteins is an easier task than sequencing DNA since protein sequences have few repeats or palindromes (the major source of difficulties in whole-genome assembly). However, not only are MS/MS spectra intrinsically more error-prone than DNA reads, but peptide sampling is strongly biased and results in some portions of the proteins being represented in many spectra while others are not seen at all. As a result, the observed peptides often correspond to isolated sets of overlapping spectra separated by coverage gaps or sometimes connected by only one or two spectra.

The results shown in Table 2 demonstrate that "shotgun protein sequencing" is a modification-tolerant approach applicable to protein mixtures. On the IKKb protein, 100 different amino acids were found to be modified in at least one spectrum and the whole dataset contained over a thousand spectra from hundreds of modified peptides. Nevertheless, it was possible to assemble 87% of all regions covered by at least 3 spectra and to derive de novo sequences that were over 90% correct. It was observed that errors predominantly fall into the initial/terminal regions of the contigs where there are fewer peaks to reliably call amino acids. Similar results were obtained on the venom dataset even though it contained almost 3000 different peptides from a mixture of crotalus atrox venom proteins. This 3.5-fold increase in the number of different peptides did not affect the sequencing accuracy and resulted in a 2-fold increase in the number of sequenced amino acids (IKKb vs. venom). Although the total length of all proteins identified on the venom dataset is approximately 4 times that of the IKKb protein, much of the additional peptide diversity in the former is actually coming from the same protein regions. This is evidenced both by a larger number of peptides per contig and by the increase in sequencing coverage—more peptides per contig lead to an increased probability of finding spectrum peaks for all amino acids.

The majority of all contig sequences was readily identifiable as a peptide from the corresponding database –84% for the IKKb dataset and 70% for the venom dataset. However, the latter also resulted in a significant number of contig sequences that did not match any proteins from the target species but had a significant match to other related species when matched against the database (using blastp and SPIDER). These are listed in Table 3 as homologous peptides and represent 14% of all de novo sequences obtained in the venom dataset.

TABLE 3

| De novo sequence | Homologous matches | Homologous protein | Species |
|---|---|---|---|
| L(TP)GSQCAD(GV)CCDQCRF[Q,K] (SEQ ID NO. 1) | LTPGSQCADGVCCDQCRFT (SEQ ID NO. 2) | O42138 | Agkistrodon contortrix laticinctus |
|  | LRPGSQCAEGMCCDQCRFM (SEQ ID NO. 3) | Q2QA03 | Crotalus durissus durissus |
|  | LRPGAQCADGLCCDQCRFI (SEQ ID NO. 4) | P68520 | Crotalus atrox |
| KVLNEDEQTRD(PK) (SEQ ID NO. 5) | KVLNEDEQTRKPK (SEQ ID NO. 6) | Q9DF66 | Trimeresurus jerdonii |
|  | KVPNEDEQTRNPK (SEQ ID NO. 7) | Q8QHK2 | Crotalus atrox |
| (LTNCSPK)(TD)IYSYSWKR (SEQ ID NO. 8) | LTNCSPKTDIYSYSWKR (SEQ ID NO. 8) | Q71QE8 | Crotalus viridis viridis |
| Y(MF)(YL)DFLCTDPSEKC (SEQ ID NO. 9) | YMFYLDFLCTDPSEK (SEQ ID NO. 10) | Q71QE8 | Crotalus viridis viridis |

TABLE 3-continued

| De novo sequence | Homologous matches | Homologous protein | Species |
|---|---|---|---|
| (IVS)WGGDI(CA)Q(PH)EPGVY(TK) (SEQ ID NO. 11) | IVSWGGDICAQPHEPGHYTK (SEQ ID NO. 12) | Q91961 | *Agkistrodon acutus* |
| | IVSWGGDPCAQPREPGVYTK (SEQ ID NO. 13) | Q71QH8 | *Trimeresurus stejnegeri* |
| | IVSWGGDICAQPREPEPYTK (SEQ ID NO. 14) | Q2QA04 | *Crotalus durissus durissus* |

For 19 out of the 28 homologous contigs, the assembled spectra could also be identified by database search (i.e., the peptide existed in a protein from a different species) and the found peptides matched the de novo sequence. On the remaining 9 cases, the assembled spectra did not match any peptide in the database and thus this step neither confirmed nor refuted the putative homologies. All of these novel homologies were derived from contigs assembling multiple peptides where the annotated MS/MS spectra strongly supported the recovered sequences. It should also be noted that all *crotalus atrox* homologies were either matched to a different snake species or could be explained by single nucleotide polymorphisms of the original sequences, which were also detected in the sample.

Together with the 13 homologous peptides that matched only venom proteins from other species, these results suggest that some *crotalus atrox* venom proteins still remain unknown. Moreover, all homologous peptides were found among proteins from other snakes thus reinforcing our predictions.

In addition to homologous peptides, some contig sequences showed no similarity to any peptide in UniProtKB. Further, these contigs contained only spectra that were not identified by traditional database search of the individual spectra. In the venom dataset, 6 out of 18 such unidentified contigs yielded highly reliable de novo sequences containing a long tag of 10 or more amino acids, thus again suggesting a few still unknown proteins in *crotalus atrox* venom.

A small number of the assembled contigs turned out to be incorrect (due to incorrect alignments of spectra from different peptides) or to yield mostly incorrect de novo sequences that did not match the peptide sequences assigned to the assembled spectra by traditional database search. These were mostly caused by spuriously matching both b and y peaks or high intensity unexplained peaks in the assembled spectra and account for less than 5% of all assembled contigs.

Shotgun protein sequencing according to the inventive method is a modification-tolerant approach to the interpretation of tandem mass spectra that enables de novo sequencing of protein mixtures, even on ion trap instruments. The inventive method demonstrates the feasibility of very accurate de novo sequencing of modified proteins into contigs (20 aa and longer) covering contiguous sequence regions up to 108 amino acids long. In fact, the extensive contig coverage of all regions with three or more overlapping peptides indicates that the major difficulty preventing the assembly of whole proteins is the strong bias in proteolytic digestion. Thus, one straightforward route towards the production of longer contigs is through the generation of richer peptides ladders using proteases with diminished cleavage specificity. The coverage observed in the venom dataset (based on a slightly improved digestion protocol) is already superior to the fragmented coverage of IKKb.

High-resolution mass spectrometers, such as Thermo's LTQ-Orbitrap, may further enhance the capabilities and effectiveness of the inventive method. In principle, higher mass accuracy should be directly translatable into more sensitive detection of overlaps between spectra with poor b/y-ion ladders. This increased sensitivity would be particularly relevant for the case of MS/MS spectra from highly charged (3+) peptides, which usually feature poor b/y-ion fragmentation—these peptides tend to span more than one contig and could thus serve as "connectors" between adjacent contigs.

In addition to peptide identification, the inventive method provides a new paradigm for the identification of chemical and posttranslational modifications (PTMs) without any use of a database. For example, in the context of a metaproteomics project, the inventive algorithm can analyze a sample of unknown bacteria and identify modifications characteristic for these bacteria.

Figure 3B:
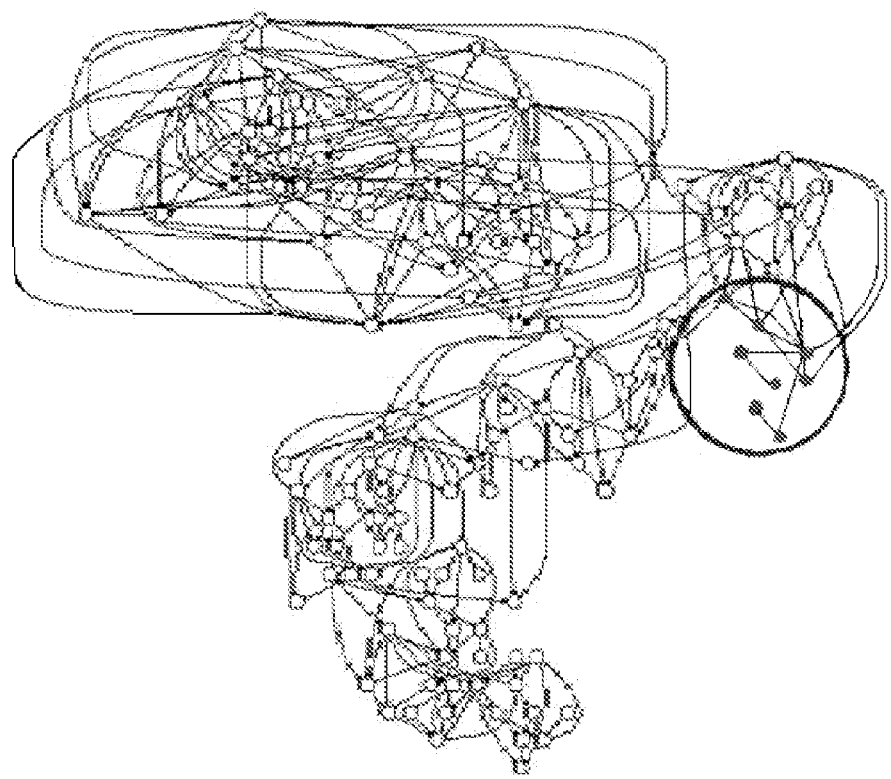
FIG. 3b shows a spectral network for the protein.

In another aspect of the inventive method, spectral pairs can be combined into a "spectral network" where each vertex corresponds to a spectrum and each edge to a spectral pair. FIG. 3b shows a spectral network of 945 MS/MS spectra (corresponding to different peptides from an IKKb protein sample illustrated in FIG. 3a) (SEQ. ID NO. 17), illustrating the key advantage of spectral networks over the traditional MS/MS database search. The traditional approach considers each of these spectra separately without attempting to correlate different spectra from related peptides. As a result, the important insights that can be derived from the structure of the spectral network are lost. The inventive approach consolidates all of these spectra into 117clusters (vertices of the network) and reveals many spectral pairs (edges of the network). This results in the analysis of all spectra "at once" and thus increases the confidence of peptide identifications, reinforces predictions of modifications by using correlated spectra, and eliminates the need to "guess" modifications in advance. Moreover, the spectral network allows these spectra to be assembled into an intact 34 amino acid long segment of the IKKb protein, thus opening the door toward shotgun protein sequencing.

Spectral networks can also make a contribution toward detection of rare modifications. Such modifications usually occur on only a very small number of peptides and are thus unlikely to be detected by the PTM frequency matrix approach. Furthermore, these can co-occur with other more frequent modifications and thus completely escape identification. These cases can be addressed by focusing on modification networks, which are subnetworks of the spectral network connecting multiple modification states of the same peptide.

The modification networks approach to PTM identification can be demonstrated using the Lens dataset (also studied by Tsur et al. (*Nat. Biotechnol.*, 23:1562-1567, 2005) among others.) The Lens dataset consists of 27,154 MS/MS spectra from a trypsin digestion of lenses from a 93 year-old male (spectra were obtained on a ThermoFinnigan LCQ Classic ion trap mass spectrometer). Lens proteins, due to a very low turnover, tend to accumulate many posttranslational modifications over time and often result in increased opaqueness and cataracts. This dataset has been extensively studied, resulting in the identification of 416 unmodified peptides and 450 modified peptides. Furthermore, 318 unmodified peptides had spectral pairs and 343 modified peptides had an unmodified version in the sample.

As an initial preprocessing step, low quality spectra were removed using an approach similar to Bern et al. (*Bioinformatics*, 20 Suppl. 1:49-49, 2004, incorporated herein by reference.) Applying the previously-described clustering procedure to the remaining spectra identified 938 clusters (including 6319 spectra) and obtained a combined dataset of 11,932 spectra (938 clustered spectra and 10,994 non-clustered spectra). Out of these, 2001 spectra were found to be paired, resulting in the identification of 280 unmodified peptides. (88% of all unmodified peptides that have some pair in the dataset).

Although at a first glance the number of annotations (280) may seem small when compared to the number of paired spectra (2001), it should be noted that many of these paired spectra come from modified peptides and thus may not generate long enough tags to match the correct peptide in the database. However, most spectra from modified peptides were correctly paired with their unmodified counterpart and were thus already linked to the correct peptide. Additionally, the spectral alignment between any two spectra promptly provides both the location and mass of the modification. Thus, suppose that an identified spectrum S was annotated with a peptide $p_1 \ldots p_n$ and paired with a non-annotated spectrum S'. Using the inventive spectral alignment approach, one can determine on which amino acid $p_i$ the modification occurred and readily annotate S' with $p_1 \ldots p_{i-1} p_i^* p_{i+1} \ldots p_n$, where p* stands for a modification of $p_i$. This operation is defined as the propagation of a peptide annotation via spectral pairs. In order to use propagation on any given spectral network, two additional conditions must be considered: (i) some non-annotated spectra may not be directly connected to an annotated spectrum (e.g., spectra with two modifications); and (ii) some non-annotated spectra may be connected to multiple annotated spectra (e.g., different prefix/suffix variants). An iterative procedure is used in each step to propagate peptide annotations from every annotated spectrum onto all its non-annotated neighbors. If a non-annotated spectrum happens to gain more than one putative annotation, the annotation that best explains the spectrum is selected.

Figure 5B:
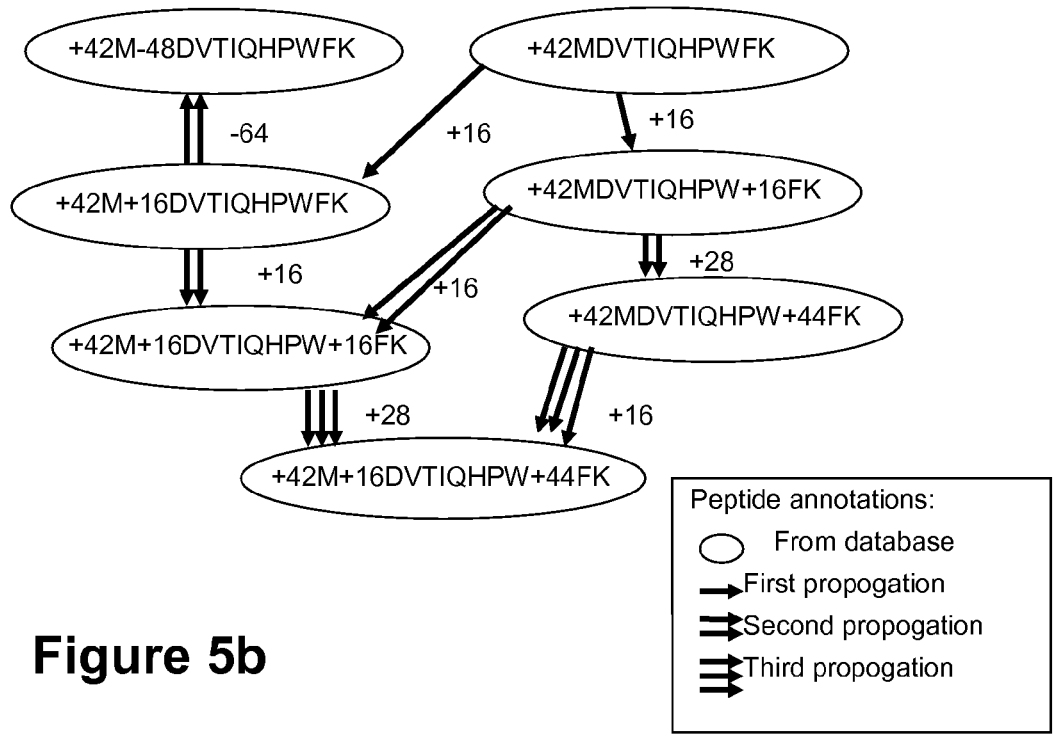
FIG. 5b is a diagram of iterative modifications.

The neighbors are then marked as annotated and are allowed to propagate their annotations on the next iteration. This procedure terminates when there are no more annotated spectra paired with non-annotated spectra. For example, the propagation procedure starts from 58 (out of 117) annotations of unmodified peptides in the spectral network shown in FIG. 3b, adds 53 annotations with a single modification on the next iteration, and finally adds 6 annotations with 2 modifications on the final iteration. FIG. 5b illustrates this iterative propagation on the Lens dataset with the modification network for peptide MDVTIQHPWFK (SEQ. ID NO. 18). The upper right node was annotated as peptide +42MDVTIQHPWFK by database search of the tag VTIQHP (SEQ. ID NO. 19); the remaining nodes were annotated by iterative propagation. On each propagation, the source peptide annotation is combined with the modification determined by the spectral product to yield a new peptide annotation.

Existing peptide identification tools have difficulty identifying and validating peptides with multiple modifications. Modification networks open up the possibility of reliably identifying such heavily modified peptides (which may be common in heavily modified proteins involved in cell signaling such as the IKK complex) via cross-validation with other modified peptides as exemplified in FIG. 5b.

Overall, the spectral networks analysis of the Lens dataset found all but one of the modification types previously identified by blind database search and provided evidence for six previously undetected modifications types. All of these new putative modification types occur on peptides that had been previously identified in this dataset, however, most of these modifications are rare in that they occur only at specific sites and thus tend to have low spectral counts, which is the primary reason these are hard to detect through blind database search. By independently comparing each MS/MS spectrum against a database, blind database search generates many false positives that are usually filtered by requiring a minimum number of occurrences of each modification. While a successful approach in detecting multiple site modifications, this may lead to difficulties in the detection of single site and less common modifications.

The spectral networks approach remedies this limitation of blind database search by being more selective in the assignment of modified peptide annotations. Spectral pairs provide additional evidence that two spectra were derived from the same peptide (in the form of correlated ion peaks and intensities) and thus add significance to otherwise difficult spectrum identifications. As illustrated in FIG. 5, this increased sensitivity is particularly evidenced on modification networks by the grouping of multiple spectra from different modification states of the same peptide.

The above-described methods for correlating between MS/MS spectra of modified and unmodified peptides greatly reduce noise in individual MS/MS spectra and, thus, make de novo interpretations so reliable that they can used in place of time consuming matching of spectra against databases. The correlated spectral content on modification networks can provide consistent evidence to support the identification of rare modifications and highly modified peptides.

Tandem mass spectra are inherently noisy and mass spectrometrists have long been trying to reduce the noise and achieve reliable de novo interpretations by advancing both instrumentation and experimental protocols. An important difference between the inventive method and prior art labeling techniques is that, instead of trying to introduce a specific modification in a controlled fashion, multiple modifications that are naturally present in the sample are exploited. The spectral networks approach allows one to decode these modifications without knowing in advance what they are and thus provide a computational, rather than instrumentation-based, solution to the problem of MS/MS spectra identification.

The inventive method provides the ability to generate rich spectral networks by intentionally subjecting samples to chemical damage. Although subjecting a sample to chemical damage seems counterintuitive from the experimental perspective, such an approach leads to significant computational advantages. Possibly the easiest way to induce chemical damage is to warm the sample in a urea solution, or to bring it into mildly acidic pH and add a large concentration of hydrogen peroxide. Also, to create a mixture of modified and unmodified peptides, one can split the sample in half, chemically damage one half, then recombine the halves for further processing.

It will be evident that there are additional embodiments that are not illustrated and/or described in the specification and drawings but that are clearly within the scope and spirit of the present invention. The foregoing description and accompanying drawings are, therefore, intended to be exemplary only, and the scope of the invention is to be limited solely by the appended claims.

The invention claimed is:

1. A method for interpreting peptide sequences via combination of spectra from different peptides comprising:
   providing a sample comprising a plurality of proteins;
   defining a plurality of peptide pairs wherein one peptide of the pair differs from the other peptide by a modification or mutation;
   obtaining a spectrum for each peptide of each peptide pair to form a spectral pair;
   aligning the spectra of each spectra in the spectral pair to identify signal peaks and noise peaks, wherein aligning the spectra further comprises:
      generating a spectral product matrix by mapping the two spectra onto respective x and y axes of a scatter graph;
      identifying matching peaks between the two spectra where vertical and horizontal lines extending from the peaks of each of the two spectra intersect;
      connecting pairs of adjacent matching peaks with at least one jump to form an optimal path from an origin of the scatter graph, wherein the optimal path is a longest sequence of valid jumps on the spectral product matrix; and
      identifying the matching peaks in the optimal path as signal peaks and the peaks outside the optimal path as noise peaks;
   removing the noise peaks;
   generating a de novo sequence reconstruction by combining the signal peaks for the spectral pairs;
   conducting a sequence database search with a computer comprising a processor and a memory using the de novo sequence; and
   generating an output comprising results of the sequence database search.

2. The method according to claim 1, wherein the at least one jump is selected from a group consisting of: a horizontal or vertical jump, a diagonal jump, and an oblique jump.

3. The method according to claim 2, wherein the horizontal or vertical jump occurs during a prefix or suffix spectral alignment, and wherein the diagonal jump occurs during a modified or unmodified spectral alignment, and wherein the oblique jump occurs during a partial-overlap spectral alignment.

4. The method according to claim 1, further comprising, prior to generating a de novo sequence, clustering the spectra of each spectral pair into a spectral star to separate prefix and suffix ladders of the spectra.

5. The method according to claim 1, wherein peptide sequences of the peptide pairs are not known.

6. The method according to claim 1, further comprising, before defining a plurality of peptide pairs, introducing chemical damage to a portion of the sample to produce modified peptides.

7. The method according to claim 6, wherein the modification is caused by a chemical reaction.

8. The method according to claim 6, wherein the modification is caused by an enzyme.

9. The method according to claim 1, wherein the peptide is a member of a mixture.

10. The method according to claim 1, further comprising identifying modifications by:
- combining the spectral pairs into a spectral network having a plurality of vertices wherein each vertex corresponds to one spectrum and each edge to one spectral pair;
- analyzing each spectral pair of the network to identify modifications;
- annotating unmodified peptides within the spectral pairs;
- propagating annotated peptides by pairing annotated spectra with non-annotated spectra to identify modifications between the annotated/non-annotated spectral pair;
- repeating the steps of annotating and propagating until all spectra are annotated; and
- generating an output comprising annotations of the peptides.

11. A method for identifying proteins using mass spectrometry, comprising:
- defining a plurality of peptide pairs wherein one peptide of the pair differs from the other peptide by a modification, mutation or extension;
- obtaining a spectrum for each peptide of each peptide pair to form a spectral pair;
- aligning the spectra of each spectra in the spectral pair to identify signal peaks and noise peaks, wherein aligning the spectra further comprises:
  - generating a spectral product matrix by mapping the two spectra onto respective x and y axes of a scatter graph;
  - identifying matching peaks between the two spectra where vertical and horizontal lines extending from the peaks of each of the two spectra intersect;
  - connecting pairs of adjacent matching peaks with at least one jump to form an optimal path from an origin of the scatter graph, wherein the optimal path is a longest sequence of valid jumps on the spectral product matrix; and
  - identifying the matching peaks in the optimal path as signal peaks and the peaks outside the optimal path as noise peaks;
- removing the noise peaks;
- generating a consensus sequence reconstruction by combining the separated signal peaks for the spectral pairs;
- conducting a database search using the consensus sequence; and
- generating an output comprising results of the database search.

12. The method according to claim 11, further comprising:
identifying protein modifications by comparing the consensus sequence reconstruction and sequence variants detected by spectral pairs.

13. The method according to claim 11, wherein the at least one jump is selected from a group consisting of: a horizontal or vertical jump, a diagonal jump, and an oblique jump.

14. The method according to claim 13, wherein the horizontal or vertical jump occurs during a prefix or suffix spectral alignment, and wherein the diagonal jump occurs during a modified or unmodified spectral alignment, and wherein the oblique jump occurs during a partial-overlap spectral alignment.

15. The method according to claim 11, further comprising, prior to generating a consensus sequence, clustering the spectra of each spectral pair into a spectral star to separate prefix and suffix ladders of the spectra.

16. The method according to claim 11, wherein peptide sequences of the peptide pairs are not known.

17. The method according to claim 11, further comprising, before defining a plurality of peptide pairs, introducing chemical damage to a portion of the sample to produce modified peptides.

18. The method according to claim 17, wherein the modification is caused by a chemical reaction.

19. The method according to claim 17, wherein the modification is caused by an enzyme.

20. The method according to claim 11, wherein the peptide is a member of a mixture.

21. The method according to claim 11, further comprising identifying modifications by:
- combining the spectral pairs into a spectral network having a plurality of vertices wherein each vertex corresponds to one spectrum and each edge to one spectral pair;
- analyzing each spectral pair of the network to identify modifications;
- annotating unmodified peptides within the spectral pairs;
- propagating annotated peptides by pairing annotated spectra with non-annotated spectra to identify modifications between the annotated/non-annotated spectral pair;
- repeating the steps of annotating and propagating until all spectra are annotated; and
- generating an output comprising annotations of the peptides.

22. A method of computationally increasing signal to noise ratio in tandem mass spectra, comprising:
- obtaining a first set of mass spectra of a peptide;
- causing a modification to a segment of said peptide;
- obtaining second set of mass spectra of the modified peptide;
- generating pairs of mass spectra from the first and second sets of mass spectra;
- aligning the spectra of each spectra in the spectral pair to identify signal peaks and noise peaks, wherein aligning the spectra further comprises:
  - generating a spectral product matrix by mapping the two spectra onto respective x and y axes of a scatter graph;
  - identifying matching peaks between the two spectra where vertical and horizontal lines extending from the peaks of each of the two spectra intersect;
  - connecting pairs of adjacent matching peaks with at least one jump to form an optimal path from an origin of the scatter graph, wherein the optimal path is a longest sequence of valid jumps on the spectral product matrix; and
  - identifying the matching peaks in the optimal path as signal peaks and the peaks outside the optimal path as noise peaks;
- removing the noise peaks;
- combining the separated signal peaks to produce a consensus spectrum; and
- generating an output comprising the consensus spectrum.

* * * * *

SEQUENCE LISTING

<160> NUMBER OF SEQ ID NOS: 26

<210> SEQ ID NO 1
<211> LENGTH: 19
<212> TYPE: PRT
<213> ORGANISM: Artificial Sequence
<220> FEATURE:
<223> OTHER INFORMATION: de novo peptide sequence reconstruction from
      MS/MS spectra
<220> FEATURE:
<221> NAME/KEY: MISC_FEATURE
<222> LOCATION: (19)..(19)
<223> OTHER INFORMATION: Xaa can be Gln or Lys

<400> SEQUENCE: 1

Leu Thr Pro Gly Ser Gln Cys Ala Asp Gly Val Cys Cys Asp Gln Cys
1               5                   10                  15

Arg Phe Xaa

<210> SEQ ID NO 2
<211> LENGTH: 19
<212> TYPE: PRT
<213> ORGANISM: Agkistrodon contortrix laticinctus

<400> SEQUENCE: 2

Leu Thr Pro Gly Ser Gln Cys Ala Asp Gly Val Cys Cys Asp Gln Cys
1               5                   10                  15

Arg Phe Thr

<210> SEQ ID NO 3
<211> LENGTH: 19
<212> TYPE: PRT
<213> ORGANISM: Crotalus durissus durissus

<400> SEQUENCE: 3

Leu Arg Pro Gly Ser Gln Cys Ala Glu Gly Met Cys Cys Asp Gln Cys
1               5                   10                  15

Arg Phe Met

<210> SEQ ID NO 4
<211> LENGTH: 19
<212> TYPE: PRT
<213> ORGANISM: Crotalus atrox

<400> SEQUENCE: 4

Leu Arg Pro Gly Ala Gln Cys Ala Asp Gly Leu Cys Cys Asp Gln Cys
1 5 10 15

Arg Phe Ile

<210> SEQ ID NO 5
<211> LENGTH: 13
<212> TYPE: PRT
<213> ORGANISM: Artificial Sequence
<220> FEATURE:
<223> OTHER INFORMATION: de novo peptide reconstruction from MS/MS spectra

<400> SEQUENCE: 5

Lys Val Leu Asn Glu Asp Glu Gln Thr Arg Asp Pro Lys
1 5 10

<210> SEQ ID NO 6
<211> LENGTH: 13

```
<212> TYPE: PRT
<213> ORGANISM: Trimeresurus jerdonii

<400> SEQUENCE: 6

Lys Val Leu Asn Glu Asp Glu Gln Thr Arg Asp Pro Lys
1               5                   10

<210> SEQ ID NO 7
<211> LENGTH: 13
<212> TYPE: PRT
<213> ORGANISM: Crotalus atrox

<400> SEQUENCE: 7

Lys Val Pro Asn Glu Asp Glu Gln Thr Arg Asn Pro Lys
1               5                   10

<210> SEQ ID NO 8
<211> LENGTH: 17
<212> TYPE: PRT
<213> ORGANISM: Crotalus viridis viridis

<400> SEQUENCE: 8

Leu Thr Asn Cys Ser Pro Lys Thr Asp Ile Tyr Ser Tyr Ser Trp Lys
1               5                   10                  15

Arg

<210> SEQ ID NO 9
<211> LENGTH: 16
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 9

Tyr Met Phe Tyr Leu Asp Phe Leu Cys Thr Asp Pro Ser Glu Lys Cys
1               5                   10                  15

<210> SEQ ID NO 10
<211> LENGTH: 15
<212> TYPE: PRT
<213> ORGANISM: Crotalus viridis viridis

<400> SEQUENCE: 10

Tyr Met Phe Tyr Leu Asp Phe Leu Cys Thr Asp Pro Ser Glu Lys
1               5                   10                  15

<210> SEQ ID NO 11
<211> LENGTH: 20
<212> TYPE: PRT
<213> ORGANISM: Artificial Sequence
<220> FEATURE:
<223> OTHER INFORMATION: de novo peptide reconstruction from
      MS/MS spectra

<400> SEQUENCE: 11

Ile Val Ser Trp Gly Gly Asp Ile Cys Ala Gln Pro His Glu Pro Gly
1               5                   10                  15

Val Tyr Thr Lys
            20

<210> SEQ ID NO 12
<211> LENGTH: 20
<212> TYPE: PRT
<213> ORGANISM: Agkistrodon acutus
```

```
<400> SEQUENCE: 12

Ile Val Ser Trp Gly Gly Asp Ile Cys Ala Gln Pro His Glu Pro Gly
1               5                   10                  15

His Tyr Thr Lys
            20

<210> SEQ ID NO 13
<211> LENGTH: 20
<212> TYPE: PRT
<213> ORGANISM: Trimeresurus stejnegeri

<400> SEQUENCE: 13

Ile Val Ser Trp Gly Gly Asp Pro Cys Ala Gln Pro Arg Glu Pro Gly
1               5                   10                  15

Val Tyr Thr Lys
            20

<210> SEQ ID NO 14
<211> LENGTH: 20
<212> TYPE: PRT
<213> ORGANISM: Crotalus durissus durissus

<400> SEQUENCE: 14

Ile Val Ser Trp Gly Gly Asp Ile Cys Ala Gln Pro Arg Glu Pro Glu
1               5                   10                  15

Pro Tyr Thr Lys
            20

<210> SEQ ID NO 15
<211> LENGTH: 5
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 15

Thr Glu Val Met Ala
1               5

<210> SEQ ID NO 16
<211> LENGTH: 7
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 16

Thr Glu Val Met Ala Phe Arg
1               5

<210> SEQ ID NO 17
<211> LENGTH: 16
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 17

Lys Gln Gly Gly Thr Leu Asp Asp Leu Glu Glu Gln Ala Arg Glu Leu
1               5                   10                  15

<210> SEQ ID NO 18
```

```
<211> LENGTH: 11
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 18

Met Asp Val Thr Ile Gln His Pro Trp Phe Lys
1               5                   10

<210> SEQ ID NO 19
<211> LENGTH: 6
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 19

Val Thr Ile Gln His Pro
1               5

<210> SEQ ID NO 20
<211> LENGTH: 10
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 20

Ser Val Ser Cys Ile Leu Gln Glu Pro Lys
1               5                   10

<210> SEQ ID NO 21
<211> LENGTH: 12
<212> TYPE: PRT
<213> ORGANISM: Artificial Sequence
<220> FEATURE:
<223> OTHER INFORMATION: de novo peptide sequence reconstruction from
      MS/MS

<400> SEQUENCE: 21

Pro Glu Ser Val Ser Cys Ile Leu Gln Glu Pro Lys
1               5                   10

<210> SEQ ID NO 22
<211> LENGTH: 7
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 22

Ser Val Ser Cys Ile Leu Gln
1               5

<210> SEQ ID NO 23
<211> LENGTH: 3
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 23

Glu Pro Lys
```

```
<210> SEQ ID NO 24
<211> LENGTH: 11
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 24

Ser Val Ser Cys Ile Leu Gln Glu Pro Lys Arg
1               5                   10

<210> SEQ ID NO 25
<211> LENGTH: 25
<212> TYPE: PRT
<213> ORGANISM: Crotalus Atrox Catracollastatin

<400> SEQUENCE: 25

Phe Ser Lys Ser Gly Thr Glu Cys Arg Ala Ser Met Ser Glu Cys Asp
1               5                   10                  15

Pro Ala Glu His Cys Thr Gly Gln Ser
            20                  25

<210> SEQ ID NO 26
<211> LENGTH: 9
<212> TYPE: PRT
<213> ORGANISM: Artificial Sequence
<220> FEATURE:
<223> OTHER INFORMATION: de novo peptide sequence reconstruction from
      MS/MS spectra

<400> SEQUENCE: 26

Ser Glu Glu Leu Val Ala Glu Ala His
1               5
```